(12) United States Patent
Avni

(10) Patent No.: US 9,114,224 B2
(45) Date of Patent: Aug. 25, 2015

(54) DEVICE AND METHODS FOR APPLYING THERAPEUTIC PROTOCOLS TO ORGANS OF THE CARDIOPULMONARY SYSTEM

(75) Inventor: Yuval Avni, Jaffa-Tel Aviv (IL)

(73) Assignee: RESPINOVA LTD., Herzliya Pituach (IL)

( * ) Notice: Subject to any disclaimer, the term of this patent is extended or adjusted under 35 U.S.C. 154(b) by 642 days.

(21) Appl. No.: 13/377,087

(22) PCT Filed: Oct. 11, 2009

(86) PCT No.: PCT/IL2009/000962
§ 371 (c)(1),
(2), (4) Date: Jan. 13, 2012

(87) PCT Pub. No.: WO2011/007346
PCT Pub. Date: Jan. 20, 2011

(65) Prior Publication Data
US 2012/0103337 A1   May 3, 2012

Related U.S. Application Data

(60) Provisional application No. 61/185,230, filed on Jun. 9, 2009.

(51) Int. Cl.
*A61M 16/12* (2006.01)
*A61M 21/02* (2006.01)
(Continued)

(52) U.S. Cl.
CPC ........... *A61M 16/12* (2013.01); *A61M 16/0006* (2014.02); *A61M 21/02* (2013.01);
(Continued)

(58) Field of Classification Search
CPC . A61M 16/0006; A61M 21/02; A61M 16/12; A61M 16/00; A61M 1/00; A61M 1/0066; A61M 16/0057; A61M 16/0009; A61M 16/0096; A61M 15/08; A61M 15/0085; A61M 11/00; A61M 15/00; A61M 16/107; A61M 16/0051; A61M 16/0063; A61M 16/10; A61M 15/0065; A61M 15/0086; A61M 15/0035; A61M 15/0003; A61M 15/0016; A61M 15/002; F16K 11/076; A61H 1/00; A61H 15/0085; A61H 23/0254; A61K 31/495; A61K 36/61; A61K 38/28; A61B 5/087; A61B 18/18; A61B 17/00; A61B 8/12; A61B 18/1477; A61B 18/1492; A61B 18/1815; A61B 18/24; A62B 7/00; A62B 9/00
USPC ............. 128/200.24, 200.26, 204.18, 204.21, 128/204.23, 205.11, 205.23, 205.24, 128/206.21, 207.14, 207.16
See application file for complete search history.

(56) References Cited

U.S. PATENT DOCUMENTS 5,211,171 A * 5/1993 Choromokos ........... 128/205.19
5,603,315 A    2/1997 Sasso, Jr.
(Continued)

OTHER PUBLICATIONS

International Search Report and Written Opinion dated Feb. 4, 2010 in corresponding International Application No. PCT/IL2009/000962.
(Continued)

*Primary Examiner* — Annette Dixon
(74) *Attorney, Agent, or Firm* — The Law Office of Michael E. Kondoudis

(57) ABSTRACT

A device for the introduction of a fluid into a human's airway. The air so introduced has a carefully modulated envelope of pressure vs. time. The envelope generally includes sequences of pressurized air packets of controlled frequency and pressures. The device produces the packets using pressurized air occluded by a shutter action that "chops" and interrupts the fluid stream. The vibrations induced by the device within human organs have been shown to have beneficial effects on various bodily systems, such as an increase in heart rate variability, an increase in absorbed oxygen, and a decrease in absorbed CO2.

21 Claims, 11 Drawing Sheets

(51) Int. Cl.
  *A61M 16/00* (2006.01)
  *A61M 16/10* (2006.01)
  *A61M 21/00* (2006.01)

(52) U.S. Cl.
  CPC .... *A61M16/0066* (2013.01); *A61M 2016/0027* (2013.01); *A61M 2016/103* (2013.01); *A61M 2016/1035* (2013.01); *A61M 2021/0088* (2013.01); *A61M 2202/0208* (2013.01); *A61M 2202/0275* (2013.01); *A61M 2205/50* (2013.01); *A61M 2205/52* (2013.01); *A61M 2230/04* (2013.01); *A61M 2230/205* (2013.01); *A61M 2230/30* (2013.01)

(56) References Cited

U.S. PATENT DOCUMENTS

| | | | |
|---|---|---|---|
| 5,862,802 | A | 1/1999 | Bird |
| 6,415,797 | B1 | 7/2002 | Groth et al. |
| 6,934,571 | B2 | 8/2005 | Wiesmann et al. |
| 7,165,547 | B2 | 1/2007 | Truitt et al. |
| 7,270,638 | B2 | 9/2007 | Lundberg et al. |
| 7,314,046 | B2 | 1/2008 | Schroeder et al. |
| 8,051,854 | B2 * | 11/2011 | Faram ............... 128/204.25 |
| 2002/0104535 | A1 * | 8/2002 | Biondo et al. ........ 128/204.21 |
| 2005/0016530 | A1 | 1/2005 | McCutcheon et al. |
| 2005/0066968 | A1 | 3/2005 | Shofner et al. |
| 2008/0156319 | A1 | 7/2008 | Avni |
| 2008/0200848 | A1 * | 8/2008 | Avni ............................ 601/46 |
| 2009/0178672 | A1 * | 7/2009 | Mullinger et al. ....... 128/200.14 |
| 2009/0306644 | A1 * | 12/2009 | Mayse et al. ................... 606/33 |
| 2012/0247466 | A1 * | 10/2012 | Avni ........................ 128/203.15 |

OTHER PUBLICATIONS

International Preliminary Report on Patentability dated Aug. 1, 2011 in corresponding International Application No. PCT/IL2009/000962.

Koiwa et al., Modification of Human Left Ventricular Relaxation by Small-Amplitude, Phase-Controlled Mechanical Vibration on the Chest Wall, Circulation, 1997, pp. 156-162, vol. 95, American Heart Association, Inc.

Takagi et al., Diastolic vibration improves systolic function in cases of incomplete relaxation, Circulation, 1992, pp. 1955-1964, vol. 86, American Heart Association, Inc.

Nakayama et al., Benefit of in-phase chest wall vibration on the pulmonary hemodynamics in patients with chronic obstructive pulmonary disease, Respirology, Dec. 1998, pp. 235-240, vol. 3, No. 4.

Jiao et al., Effect of different vibration frequencies on heart rate variability and driving fatigue in healthy drivers, Int Arch Occup Environ Health, 2004, pp. 205-212, vol. 77.

\* cited by examiner

DEVICE AND METHODS FOR APPLYING THERAPEUTIC PROTOCOLS TO ORGANS OF THE CARDIOPULMONARY SYSTEM

This application is a national stage entry of international application no. PCT/IL2009/000962.

FIELD OF THE INVENTION

The present invention generally relates to a device and method for treating respiratory disorders.

BACKGROUND OF THE INVENTION

Asthma and COPD (chronic obstructive pulmonary disease) affect more than 44 million Americans. These chronic conditions require lifetime therapy. The mainstay of treatment today focuses on systemic medications, local (inhaler) therapies, oxygen therapy and mucous clearing devices. Methods of respiratory support as well as intrapulmonary percussive treatments have been employed for airway clearance and relief, but no devices or methods have been provided which are designed for delivering specific sequences of specific frequencies targeted to elicit beneficial effects in a patient according to the characteristics of the patient's illness as described herein.

To date the therapeutic impact of intrapulmonary percussive devices has not been significant enough for such technology to become standard care.

The device relates to means and methods of causing vibrations in the chest wall, amongst other effects. Some of the known effects of such vibrations are summarized below.

Koiwa et. al showed that vibrations over the chest wall at 50 Hz, that were phase controlled, i.e., activated from the onset of isovolumic relaxation to end-diastole, caused a relaxation of the left ventricle, which was significantly more pronounced in heart failure and cardiomyopathy patients than in healthy patients. [Modification of Human Left Ventricular Relaxation by Small-Amplitude, Phase-Controlled Mechanical Vibration on the Chest Wall. Yoshiro Koiwa, MD; Hideyuki Honda, MD; Takehiko Takagi, MD; Jun-ichi Kikuchi, MD; Nobuo Hoshi, MD; Tamotsu Takishima, MD. Circulation. 1997; 95:156-162.]

Takagi et. al further showed that improved relaxation of the left ventricle by applying phase-controlled vibrations accelerate the LV relaxation rate and that this increased relaxation improves systolic function through the Frank-Starling mechanism. [Diastolic vibration improves systolic function in cases of incomplete relaxation. T Takagi, Y Koiwa, J Kikuchi, H Honda, N Hoshi, J P Butler and T Takishima. Circulation. 1992; 86:1955-1964]

Nakayama et. al found that in-phase vibrations (IPV) applied over the chest of COPD patients reduced their mea arterial pulmonary pressure and pulmonary vascular resistance, while increasing their PaO2 and decreasing their PaCO2 significantly. They conclude that IPV improves gas exchange and pulmonary circulation without affecting systemic circulation. [Benefit of in-phase chest wall vibration on the pulmonary hemodynamics in patients with chronic obstructive pulmonary disease. Nakayama H, Shibuya M, Kaneko N, Yamada M, Suzuki H, Arakawa M, Homma I. Respirology. 1998 December; 3(4):235-40.]

Kun Jiao el al. studied the effect of vibrations on the heart rate variability and driving fatigue of healthy volunteers. They compared the effect of 1.8 Hz, 6 Hz and no vibrations at all, and found that different vibrations caused different levels of fatigue, as measured subjectively by a questionnaire; and that different frequencies also caused different effects on the autonomic nervous system, as measured heart rate variability changes. [Effect of different vibration frequencies on heart rate variability and driving fatigue in healthy drivers. Kun Jiao, Zengyong Li, Ming Chen, Chengtao Wang, Shaohua Qi. Int Arch Occup Environ Health (2004) 77: 205-212]

U.S. Patent Application No. 20080156319 ('319) to Avni discloses a pulsating inhaler comprising a fluid oscillator providing a focused fluid column with a series of alternating high and low pressure zones, a drug dispenser adapted for releasing small and constant measures of at least one drug via the fluid column, and, at least one outlet orifice adapted to direct the focused fluid column towards the respiratory tract of a patient. The small and constant measures of the drug are delivered to the patient's lungs while its respiratory tracts are gently and continuously vibrated. As acknowledged, applying a sequence of pneumatic pulses to the patient's airways through the oral cavity results in therapeutic effects.

However, '319 does not teach protocols comprising optimal parameters efficacious in treating disorders or for uptake of medicaments.

Congestive Heart Failure (CHF) and Pulmonary Oedema, both being conditions with a significant pulmonary component, are examples of other conditions which would benefit from an improvement in means and methods for treatment.

Providing means and methods of generating and delivering discrete wave trains of different repetition frequencies and pulse amplitudes which are efficacious in treating pulmonary, cardio-pulmonary and breathing disorders which are more effective long term, more easily supervised and fine—tuned would fulfill a long felt and unmet need.

SUMMARY OF THE INVENTION

A protocol of Fluid Pressure Pulses (FPPs) useful for improving a patient's wellness is herein disclosed; the aforementioned protoal comprises sequences of individual FPPs, which are possibly different from each other. The fluid pressure pulses are administered to said patient's airway. The invention comprises protocols which can be asynchronous or synchronous, i.e., delivered in a way which may be independent of the patient's natural inspiratory cycle, cardiac cycle or other physiological functions, or dependent upon them, respectively. The above mentioned protocol may further be administered to the mouth cavity of a patient at a predetermined frequency and pressure in a predetermined manner which may be synchronous or asynchronous.

It is within provision of the invention to provide a protocol of Fluid Pressure Pulses (FPPs) useful for improving a patients wellness; said protocol comprising different sequences of individual FPPs; wherein said protocol is administered to said patient's airway synchronously or asynchronously with said patients rhythm of inspiratory cycle, cardiac cycle, or other physiological functions.

It is within provision of the invention to provide the aforementioned FPPs wherein said protocol is administered through the mouth cavity of the patient.

It is further within provision of the invention to provide the aforementioned FPPs wherein said FPPs comprise a given pressure amplitude, volume, duration and waveform; and further wherein said sequences of FPPs comprise a given frequency and duration.

It is within provision of the invention to provide an Air Delivery Device (ADD) for applying Fluid Pressure Pulses (FPPs) to airways of a patient, useful for improving a patient's wellness; each of said FPP has a given frequency, pressure amplitude, volume duration, and waveform; said ADD comprising:
a. a plurality of regulators, each of which is adapted to define a FPP with an individual frequency, pressure amplitude, volume and duration;
b. means for producing the therapeutic protocol of said defined individual FPPs;
c. mouth piece adapted to introduce said therapeutic protocol of produced FPPs within the patient's airway;
wherein said therapeutic protocol of FPPs comprises two or more different individual Sequences of FPPs.

It is within provision of the invention to provide the aforementioned ADD, wherein said therapeutic protocol comprises at least one individual Sequences of FPP.

It is further within provision of the invention to provide the aforementioned ADD, wherein said therapeutic protocol comprises at least one individual Sequences of FPP.

It is further within provision of the invention to provide the aforementioned ADD, wherein said protocol is administered to said patients contemporaneously and independently of said patient's inspirations and expirations.

It is further within provision of the invention to provide the aforementioned ADD, wherein said protocol additionally comprises at least one persistent or semi-persistent stream of fluid of predetermined oscillating frequency administered in parallel with said sequences of applied FPPs.

It is further within provision of the invention to provide the aforementioned ADD, wherein said protocol comprises N FPPs delivered for predetermined durations; N is an integer number equal or greater than 2.

It is further within provision of the invention to provide the aforementioned ADD, wherein said FPPs comprise parameters selected from a group consisting of Frequency, Pressure Amplitude, Volume waveform, and Duration.

It is further within provision of the invention to provide the aforementioned ADD, wherein said Frequency is selected from a group consisting of about 0.5 Hz to about 5.0 Hz, about 5.0 Hz to about 10 Hz, about 10 Hz to about 20 Hz, about 20 Hz to about 30 Hz, about 30 Hz to about 40 Hz, about 40 Hz to about 50 Hz, about 50 Hz to about 60 Hz, about 60 Hz to about 70 Hz, about 70 Hz to about 80 Hz, about 80 Hz to about 90 Hz, about 90 Hz to about 100 Hz, any integer multiples thereof.

It is further within provision of the invention to provide the aforementioned ADD, wherein any of said selected Frequency is delivered with its corresponding overtones, undertones, or multiples thereof.

It is further within provision of the invention to provide the aforementioned ADD, wherein said FPP pressure amplitudes are selected on the basis of clinical efficacy.

It is further within provision of the invention to provide the aforementioned ADD, wherein said FPP volumes are selected on the basis of clinical efficacy.

It is further within provision of the invention to provide the aforementioned ADD, wherein said series of predetermined fluid pressure pulses is accompanied by predetermined humming oscillations for stimulation of NO (nitric-oxide) production, said humming oscillations provided independently or contemporaneously with said series of FPPs.

It is further within provision of the invention to provide the aforementioned ADD, herein said improvement in patient wellness—mental health, physical health and quality of life, is defined by tools designed to measure wellness areas selected from the group consisting of, pulmonary function (e.g., by pulmonary function test), static lung volume (e.g., by lung plethysmography), diffusion capacity (e.g., by $D_LCO$ test), functional exercise capacity (e.g., by 6 minute walk test), drug uptake, heart function (e.g., by echo-cardiography), cardio vascular efficiency, pulmonary blood pressure, systemic blood pressure, blood oxygenation (e.g., by tepO2), NO (nitric oxide) production, Health Related Quality of Life Questionnaire (e.g., CRQ—Chronic Respiratory Disease Questionnaire) or any combination thereof.

It is further within provision of the invention to provide the aforementioned ADD, wherein said ADD is adapted for use by patients with Cystic Fibrosis.

It is further within provision of the invention to provide the aforementioned ADD, wherein said ADD is adapted for use by patients with COPD.

It is further within provision of the invention to provide the aforementioned ADD, wherein said ADD is adapted for use by patients with asthma.

It is further within provision of the invention to provide the aforementioned ADD, wherein said ADD is adapted for use for patients with sinusitis.

It is further within provision of the invention to provide the aforementioned ADD, wherein said ADD is adapted for use by patients with pneumonia.

It is further within provision of the invention to provide the aforementioned ADD, wherein said ADD is adapted for use by patients with heart failure, Congestive Heart Failure (CHF) and/or pulmonary oedema.

It is further within provision of the invention to provide the aforementioned ADD, wherein said ADD is adapted for use by patients with pulmonary hypertension.

It is further within provision of the invention to provide the aforementioned ADD, wherein said ADD is adapted for use by patients with conditions including Nasal Congestion, Emphysema, Interstitial fibrosis, Pulmonary hypertension, Sarcoidosis, COPD, Asthma, Bronchitis, asbestosis, radiation fibrosis, ARDS, Cystic Fibrosis, Sinusitis, Pharyngitis, Laryngitis, Otitis Media, Pneumonia, Lung tumors, Coronary heart disease, Cardiomyopathy (CM), Hypertrophic CM, Dilated CM, Hypertensive CM, Congestive Heart Failure, Inflammatory heart disease, Endocarditis, Myocarditis, Cardiac Arrhythmias, Atrial fibrillation, Atrial flutter, Supraventricular Tachycardia, A-V blocks, Systemic, Hypertension, Pulmonary hypertension, Atherosclerosis, Atherosclerosis of the Carotid arteries, Sleep apnea, and Fibromyalgia.

It is further within provision of the invention to provide the aforementioned ADD, wherein there is an improvement in said patients diffusion capacity as measured by the DLCO test.

It is further within provision of the invention to provide the aforementioned ADD, wherein there is an improvement in said patients wellness as measured by the 6 minute walk test It is further within provision of the invention to provide the aforementioned ADD, wherein there is an improvement in said patients wellness as measured by the incremental shuttle walking test.

It is further within provision of the invention to provide the aforementioned ADD, wherein there is an improvement in said patients lung volumes as measured by Lung Plethysmography.

It is further within provision of the invention to provide the aforementioned ADD, wherein there is an improvement in the patient's quality of life is measured by an increase in the patients score on the CRQ (Chronic Respiratory Questionnaire) scale compared to the patient's score prior to treatment.

It is further within provision of the invention to provide the aforementioned ADD, wherein there is an improvement in the patient's quality of life is measured by an increase in the patient's score of at least about 10 points on the Karnofsky scale compared to the patient's score prior to treatment.

It is further within provision of the invention to provide the aforementioned ADD wherein the improvement in the patient's lung function is measured by an increase in the patient's score of at least about 20 points on the Karnofsky scale compared to the patient's score prior to treatment.

It is further within provision of the invention to provide the aforementioned ADD wherein the improvement in the patient's quality of life is measured by an increase in the patient's score of at least about 10 points on the Karnofsky scale compared to the patient's score prior to treatment.

It is further within provision of the invention to provide the aforementioned ADD wherein the improvement in the patient's quality of life is measured by an increase in the patient's score of at least about 20 points on the Karnofsky scale compared to the patient's score prior to treatment.

It is further within provision of the invention to provide the aforementioned ADD wherein the improvement in the patient's quality of life is measured by a questionnaire selected from the group consisting of: St. George's Quality of Life Questionnaire, the Karnofsky scale, the WHO QOL questionnaire, It is further within provision of the invention to provide the aforementioned ADD wherein there is an improvement in measures of physical performance, mental performance, or both.

It is further within provision of the invention to provide the aforementioned ADD wherein the RMSSD increases by at least 20% after treatment with said ADD.

It is further within provision of the invention to provide the aforementioned ADD wherein the SDNN increases by at least 10% after treatment with said ADD.

It is further within provision of the invention to provide the aforementioned ADD wherein the PNN50 increases by at least 5% after treatment with said ADD.

It is further within provision of the invention to provide the aforementioned ADD wherein the improvement in the patient's quality of life is measured by an improvement in the patient's symptoms as defined by the Karnofsky score selected from a group comprising of Bedridden to Symptomatic in bed >50% of day, Symptomatic, in bed >50% of day to Symptomatic, in bed <50% of day, or Symptomatic, in bed <50% of day to Symptomatic, fully ambulatory, or Symptomatic, fully ambulatory to Asymptomatic, normal Function.

It is further within provision of the invention to provide the aforementioned ADD wherein said ADD additionally comprises
   a. a microprocessor for applying protocols of said FPP's;
   b. at least one sensor for measuring at least one health related parameter obtained from the patient;
   c. a database storage microprocessor for storage and updating of health related data;
   d. at least one analysing means for analysing said health related parameter obtained from patient and comparing said parameter with said health related data of said database thereby facilitating selection of an appropriate FPP administration protocol from a repertoire of said protocols for applying to said patient.

It is further within provision of the invention to provide the aforementioned ADD wherein said at least one sensor, said database storage microprocessor, said at least one analysing means and said means for producing the therapeutic protocol of FPP are operationally communicating.

It is further within provision of the invention to provide the aforementioned ADD wherein said ADD is additionally provided with a central processing unit for storage of a repertoire of protocols.

It is further within provision of the invention to provide the aforementioned ADD wherein said ADD is provided with means for feedback control of said ADD and protocol selection.

It is further within provision of the invention to provide the aforementioned ADD wherein said ADD is provided with a facemask.

It is further within provision of the invention to provide the aforementioned ADD provided with a plurality of fluid valves.

It is further within provision of the invention to provide the aforementioned ADD wherein said ADD is such the average pressure of said FPPs is increased or decreased depending on the desired effects being short term or long term, respectively.

A method for applying Fluid Pressure Pulses (FPPs) defining a therapeutic protocol of FPPs to the airways of a patient; each of said FPP is defined by a given frequency, amplitude, volume and duration, said method including the following steps:
   e. obtaining an ADD for applying Fluid Pressure Pulses (FPPs) to airways of a patient; each of said FPP has a given frequency, amplitude, volume and duration; said ADD comprising a plurality of regulators, each of which is adapted to define a FPP with an individual frequency, pressure amplitude, volume and duration; means for producing the therapeutic protocol of said defined individual FPPs; said therapeutic protocol of FPPs comprises two or more different individual FPPs; and mouthpiece adapted to introduce said therapeutic protocol of produced FFPS within the patient's airway;
   f. fitting said mouthpiece to said patient airways; and
   g. operating said ADD;
   wherein said step of operating said ADD delivers a therapeutic protocol of FPPs comprises two or more different individual FPPs.

It is further within provision of the invention to provide the aforementioned ADD wherein said method comprises delivering a therapeutic protocol of FPPs wherein said therapeutic protocol comprises at least one individual FPP.

It is further within provision of the invention to provide the aforementioned ADD said method further comprising steps of
   h. obtaining said ADD additionally comprising
     i. a microprocessor for applying administration protocols of said FPP's
     ii. at least one sensor for measuring at least one health related parameter obtained from the patient
     iii. a microprocessor containing a database concerning health related data
     iv. at least one analyzing means adapted for analyzing said health related parameter obtained from patient and comparing said parameter with said health related data of said database thereby facilitating selection of an appropriate FPP administration protocol from a repertoire of said protocols for applying to said patient.
i. operating said ADD so as to apply said FPP's to the mouth cavity of a patient and measuring said at least one health related parameter obtained from the patient
j. analysing said health parameter obtained from said patient
k. comparing said health parameter obtained from said patient with said health related data of said database
l. selecting an appropriate FPP therapeutic protocol from a repertoire of said protocols for applying to said patient and
m. operating said ADD so as to apply said selected FPP therapeutic protocol to said patient
wherein said operating delivers a therapeutic protocol of FPPs comprises two or more different individual FPPs.

It is further within provision of the invention to provide the aforementioned ADD wherein said protocol additionally comprises at least one persistent or semi persistent stream of air of predetermined oscillating frequency administered in parallel with said said sequences of applied FPPs.

It is further within provision of the invention to provide the aforementioned ADD wherein said at least one sensor, said database concerning health related data and said at least one analysing means are operationally communicating.

It is further within provision of the invention to provide the aforementioned ADD wherein said ADD is provided with a central processing unit for storage of said repertoire of protocols.

It is further within provision of the invention to provide the aforementioned ADD wherein said ADD is provided with a controller communicating with said regulators, said microprocessors and said means for producing the therapeutic protocol of FPP for feedback control of said protocol selection.

It is further within provision of the invention to provide the aforementioned ADD wherein said protocol comprises N FPPs delivered for predetermined durations of about 1 second to about 30 minutes.

It is further within provision of the invention to provide the aforementioned ADD wherein said protocol comprises N FPPs delivered for predetermined durations of about 30 minutes to about 24 hours.

It is further within provision of the invention to provide the aforementioned ADD wherein said FPPs comprise parameters selected from a group consisting of Frequency, Pressure Amplitude, Volume and Duration.

It is further within provision of the invention to provide the aforementioned ADD wherein said Frequency is selected from a group consisting of about 0.5 Hz to about 5.0 Hz, about 5.0 Hz to about 10 Hz, about 10 Hz to about 20 Hz, about 20 Hz to about 30 Hz, about 30 Hz to about 40 Hz, about 40 Hz to about 50 Hz, about 50 Hz to about 60 Hz, about 60 Hz to about 70 Hz, about 70 Hz to about 80 Hz, about 80 Hz to about 90 Hz, about 90 Hz to about 100 Hz, any integer multiples thereof.

It is further within provision of the invention to provide the aforementioned ADD wherein each said selected Frequency is delivered with its corresponding overtones or multiples thereof.

It is further within provision of the invention to provide the aforementioned ADD wherein said FPP pressure amplitudes are selected on the basis of clinical efficacy.

It is further within provision of the invention to provide the aforementioned ADD wherein said FPP volumes are selected on the basis of clinical efficacity.

It is further within provision of the invention to provide the aforementioned ADD wherein said ADD is provided with means for vibrationally modulating said FPPs.

It is further within provision of the invention to provide the aforementioned ADD wherein said ADD is provided with means for predetermined humming oscillations for stimulation of NO production, said humming oscillations provided independently or contemporaneously with said series of FPPs.

It is further within provision of the invention to provide the aforementioned ADD where the pressure of said FPPSs is modulated according to an equation selected from the group consisting of:

n. $P(t) = A\sin^{-1}(\sin(\omega_1 t)) + B \times \theta(\sin(\omega_2 t)) + C$ where $\theta(t)$ is the Heaviside step function $\theta(x) = \begin{cases} 1; & x \geq 0 \\ 0; & x < 0; \end{cases}$ o. $P(t) = A\sin^{-1}(\sin(\omega_1 t)) + B \times \theta(\sin(\omega_2 t)) + C$ p. $P(t) = A\sin^{-1}(\sin(\omega_1 T)) + B\sin^{-1}(\sin(\omega_2 t)) + C$ It is further within provision of the invention to provide the aforementioned ADD where the constants A, B, C, $\omega_1$, and $\omega_2$ are such that 0.01 Hz$\leq \omega_1 \leq$1 Hz, 0.1 Hz$\leq \omega_2 \leq$10 Hz, 10 mmHg$\leq$A$\leq$250 mmHg, 10 mmHg$\leq$B$\leq$250 mmHg, and −250 mmHg$\leq$C$\leq$250 mmHg.

It is further within provision of the invention to provide the aforementioned protocol of Fluid Pressure Pulses (FPPs) useful for improving a sportsperson's performance; said protocol comprising different sequences of individual FPPs; wherein said protocol is administered to said patient's airway synchronously or asynchronously with said patients rhythm of inspiratory cycle, cardiac cycle, or other physiological functions.

It is further within provision of the invention to provide the said protocol administered through the mouth cavity of the patient.

It is further within provision of the invention to provide the protocol wherein said FPPs comprise a given pressure amplitude, volume, duration and waveform; and further wherein said sequences of FPPs comprise a given frequency and duration.

It is further within provision of the invention to provide the aforementioned Air Delivery Device (ADD) for applying Fluid Pressure Pulses (FPPs) to airways of a patient, useful for improving a sportsperson's performance; each of said FPP has a given frequency, pressure amplitude, volume duration, and waveform; said ADD comprising:
a. a plurality of regulators, each of which is adapted to define a FPP with an individual frequency, pressure amplitude, volume and duration;
b. means for producing the therapeutic protocol of said defined individual FPPs;
c. mouth piece adapted to introduce said therapeutic protocol of produced FPPs within the patient's airway;
wherein said therapeutic protocol of FPPs comprises two or more different individual Sequences of FPPs.

It is further within provision of the invention to provide the aforementioned ADD wherein said therapeutic protocol comprises at least one individual Sequences of FPP.

It is further within provision of the invention to provide the aforementioned ADD, wherein said protocol is administered to said patients contemporaneously and independently of said patient's inspirations and expirations.

It is further within provision of the invention to provide the aforementioned ADD, wherein said protocol additionally comprises at least one persistent or semi-persistent stream of fluid of predetermined oscillating frequency administered in parallel with said sequences of applied FPPs.

It is further within provision of the invention to provide the aforementioned ADD, wherein the protocol comprises N FPPs delivered for predetermined durations; N is an integer number equal or greater than 2.

It is further within provision of the invention to provide the aforementioned ADD, wherein the FPPs comprise parameters selected from a group consisting of Frequency, Pressure Amplitude, Volume waveform, and Duration.

It is further within provision of the invention to provide the aforementioned ADD, wherein said Frequency is selected from a group consisting of about 0.5 Hz to about 5.0 Hz, about 5.0 Hz to about 10 Hz, about 10 Hz to about 20 Hz, about 20 Hz to about 30 Hz, about 30 Hz to about 40 Hz, about 40 Hz to about 50 Hz, about 50 Hz to about 60 Hz, about 60 Hz to about 70 Hz, about 70 Hz to about 80 Hz, about 80 Hz to about 90 Hz, about 90 Hz to about 100 Hz, any integer multiples thereof.

It is further within provision of the invention to provide the aforementioned ADD, wherein any of said selected Frequency is delivered with its corresponding overtones, undertones, or multiples thereof.

It is further within provision of the invention to provide the aforementioned ADD, wherein said FPP pressure amplitudes are selected on the basis of clinical efficacy.

It is further within provision of the invention to provide the aforementioned ADD, wherein said FPP volumes are selected on the basis of clinical efficacy.

It is further within provision of the invention to provide the aforementioned ADD, wherein said series of predetermined fluid pressure pulses is accompanied by predetermined humming oscillations for stimulation of NO (nitric-oxide) production, said humming oscillations provided independently or contemporaneously with said series of FPPs.

It is further within provision of the invention to provide the aforementioned ADD wherein said improvement in sportsperson's performance—mental health, physical health and quality of life, is defined by tools designed to measure fitness in areas selected from the group consisting of, pulmonary function (e.g., by pulmonary function test), static lung volume (e.g., by lung plethysmography), diffusion capacity (e.g., by $D_L CO$ test), functional exercise capacity (e.g., by 6 minute walk test), drug uptake, heart function (e.g., by echocardiography), cardio vascular efficiency, pulmonary blood pressure, systemic blood pressure, blood oxygenation (e.g., by tcpO2), NO (nitric oxide) production, Health Related Quality of Life Questionnaire (e.g., CRQ—Chronic Respiratory Disease Questionnaire) or any combination thereof.

It is a yet further purpose of the present invention to provide means and methods for a non drug treatment for the above mentioned disorders which can be applied over long durations of treatment and extended therapeutic sessions. Such means and methods are very distinct from devices which facilitate drug delivery through inhalation.

BRIEF DESCRIPTION OF THE FIGURES

In order to understand the invention and to see how it may be implemented in practice, a plurality of embodiments is adapted to now be described, by way of non-limiting example only, with reference to the accompanying drawings, in which.

DETAILED DESCRIPTION

The following description is provided, alongside all chapters of the present invention, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide an air delivery device and method of using the same.

Figure 1A:
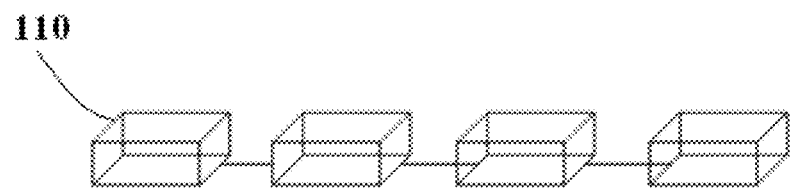
FIGS. 1a-1b are schematic views of fluid pressure pulses.
Figure 1B:
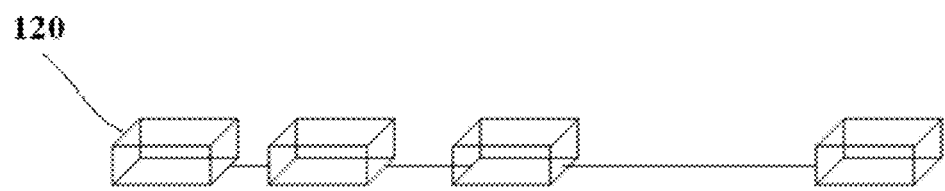
Figure 1C:
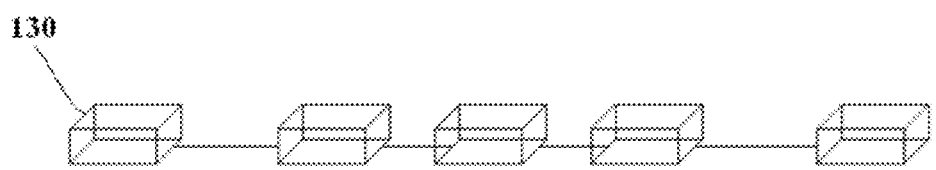
Figure 1D:
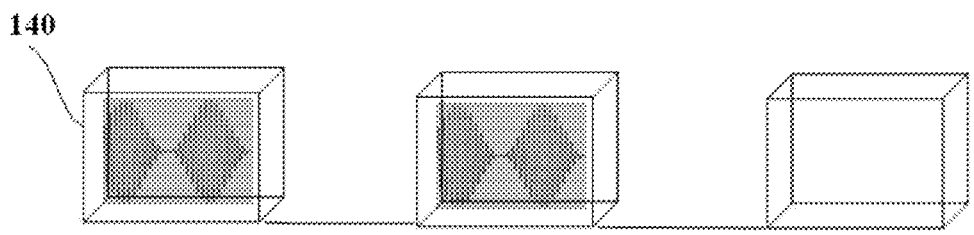

It is a core purpose of the present invention to provide disease- and symptom-specific protocols with accompanying devices, based on applying fluid (e.g., gas, air, aerosols etc.) pressure pulses (FPP) to the mouth cavity of a patient at predetermined frequencies and intervals. As shown in FIGS. 1a-1c, FPP are provided in the form of continuous pulse trains 110 (FIG. 1a) or discontinuous pulse trains 120 and 130 (FIGS. 1b and 1c). The FPPs themselves may, in some cases, be vibrationally modulated, that is to say, within each pressure pulse, representing a packet or bolus of air, different vibrations can be set up (140 in FIG. 1, represents for example the pressure as a function of time). These vibrations are in fact pressure oscillations which occur at some frequency and amplitude. It is crucial to the principal of the invention that the provided fluid pressure impulses of the invention are applied to the airway of the patient in a predetermined manner and predetermined sequence and predetermined combinations. The term "combinations" in this sense means the delivery of several frequencies simultaneously and/or consecutively, or, in musical terminology—chords and/or melodies.

The applied Protocols of FPPs may be in some embodiments synchronous and in other embodiments asynchronous, thus sometimes oppose an exhalation, and sometimes reinforce an inhalation. The patient breathes normally, whilst receiving the FPPs on inspiration and exhalation. During inspiration the supplied FPPs are in the same direction as the air being breathed in, and during exhalation the FPPs meet resistance of the air being breathed out. Both circumstances have a therapeutic effect. The rates and nature of the applied FPPs are predetermined by certain protocols of the invention, which are designed to relieve specific cardiac, pulmonary and other related conditions. Furthermore, means and methods of the invention are disclosed to enable selection of any particular protocol suitable to any particular patient and the progress of that patient's disease process during the course of treatment. The present invention supplies fluid pressure pulses (FPP) to the mouth cavity of a patient at a predetermined frequency and pressure in a predetermined manner which is not dependent upon the natural breathing rate of the patient, but in other aspects of the invention, fluid pressure pulses (FPP) are supplied to the mouth cavity of a patient at a predetermined frequency and pressure in a predetermined manner which is dependent upon the natural breathing rate of the patient. Another aspect of the invention is that means are disclosed for determining and/or supplying the fluid pressure pulses (FPPs). The aforementioned FPPs are supplied in particular sequences, tailored to the requirements of the treatment. The FPPs are in fact sequences (predetermined in some cases or adapted following feedback in other cases) of discrete pressurized air packets of controlled frequency and pressures, produced by positively or negatively pressurized air directed into the patient airway, occluded by a shutter action which "chops" and interrupts the air stream. It is understood that by pressure here is measured with respect to ambient pressure, and that negative pressure therefore refers to pressure below ambient.

In exemplary embodiments of the present invention the aforementioned FPPs are created by means of airflow occluding means (AOM) as described and illustrated herein. In the prior art, pulses of a very different type are produced, usually by pistons or impellors: in these prior art cases blasts or gusts of air are produced by the impellers and thrown forward. The variation of pressure between such blasts in these cases is less abrupt, and more wave like. Specifically, the highest frequency attained in such systems is around 2 Hz. In the prior art the specific frequencies used when applying the device clinically are not predetermined. In the prior art no specific therapeutic effect is attributed to a specific frequency.

Figure 2:
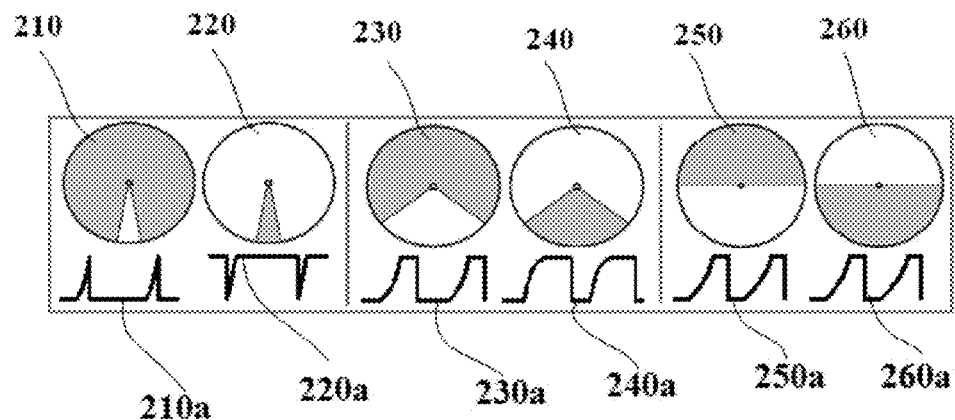
FIGS. 2 and 3 are schematic views of rotating discs and graphs of pressure profiles creating by the rotating discs.
Figure 3:
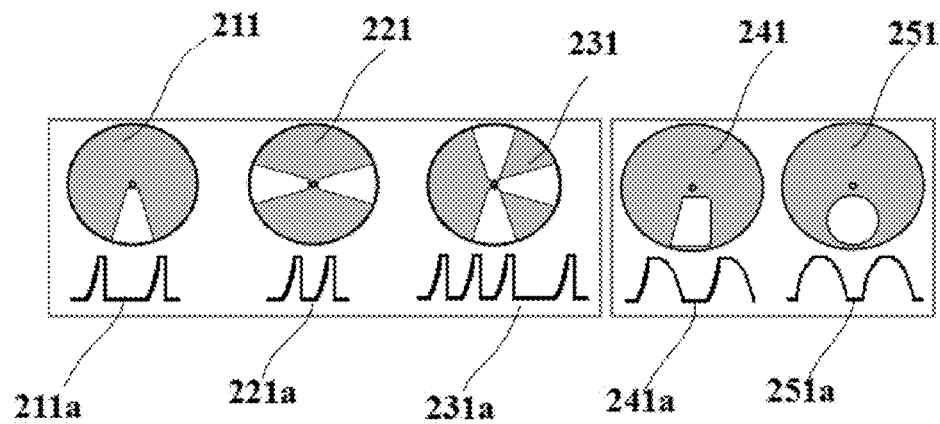
Figure 4:
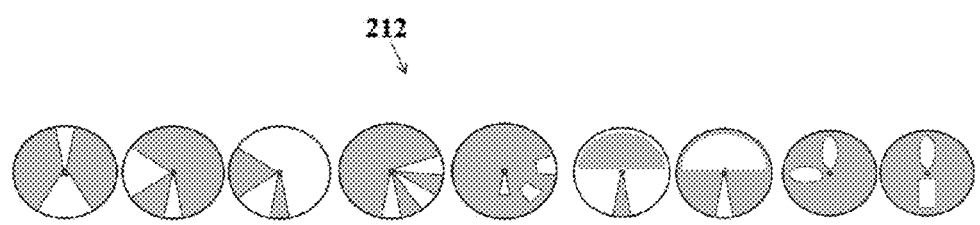
FIGS. 4 and 5 are schematic views of alternative embodiments of rotating discs.
Figure 5:
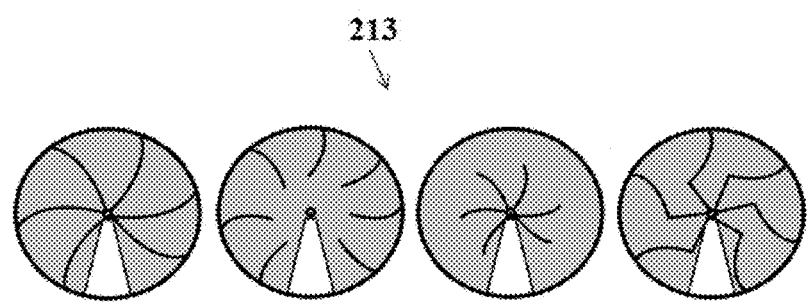

Reference is now made to FIGS. 2 and 3 schematically illustrating various designs of spinning shutter-like discs with different cutouts in them, each cutout producing an FPP of specific volume and for a specific time, followed by an interval until the next FPP is produced. The FPP pressure wave profile is illustrated beneath each disc shape. Specifically, in FIG. 2, rotating discs 210-260 create pressure wave profiles 210a-260a. Similarly, in FIG. 3, rotating discs 211-261 provide pressure wave profiles 211a-261a. Further exemplar embodiments of the invention include those illustrated schematically in FIGS. 4 and 5, which show discs 212 and 213, respectively, provided with different shaped cutouts and slits, providing variations of pressure and vibrations within a specific FPP and shaping the FPP, which, it should be again noted, is a "packet" or bolus of air introduced into the airway of the patient. Some of these embodiments are useful for providing effective drug uptake at a tissue site. Other embodiments will be useful for improving the correct physiological viscosity of mucus in CF patients. As will be obvious to one skilled in the art, other means for forming tailored pressure waveforms can be employed for purposes of the device. For example, instead of spinning discs, an electromagnetic plunger with precise position control or other suitable device such as a shutter, iris, or the like can be employed to produce the pressure waveforms of the device.

The pulses produced by the cutout shapes described above may be of almost unlimited form. As an example, a radial cutout will allow full pressure 'at once' with some inevitable delay and 'smearing' of the expected square wave due to diffusion. The resultant pressure waveform may be fit by the expression $$P(t) = P_0 \operatorname{erfc}\left(\frac{l^2}{Dt}\right)$$

where $P_0$ is a constant, D is the diffusion constant of air, t is the time, and l is the distance from pulsehaler to the point of measurement.

The FPPs may be of positive pressure relative to the ambient atmosphere, negative pressure relative to the ambient atmosphere or any dynamic combination thereof.

The sequenced flow of packets of air (the FPPs) are facilitated into the airway of the patient, in a precise sequence, combination and manner (Protocol, exemplified in table 1), which is determined e.g., by the disease or symptom to be treated. FIG. 1 illustrates schematically, and for exemplary purposes only, several of such sequences of FPPs. For example, 110 represent 4 FPPs of predetermined volume and pressure, separated by identical intervals. The boxes represent volumes of air at a certain pressure that is introduced into the patient's airway. Another sequence 120, comprises 3 FPPs separated by identical intervals, followed by a longer interval, then followed by another FPP. A further sequence, 130, is shown. The sequence of 130 comprises one FPP, followed by a long interval, followed by administration of 3 FPPs at short interval, then followed by a longer interval, followed by another FPP. The individual FPPs can themselves be amplitudinally modulated, as in 140. It can thus be seen that a myriad of protocols can be composed and administered to a patient by the means and methods of the present invention.

The protocols can be likened, by analogy, to tunes and chords made up by combinations of musical notes in a series. These 'notes' are produced by an ADD or other instrument which produces vibrating columns of air. A good analogy for the ADD would be a musical organ or similar device. Each series of notes (i.e., a musical note produced by a number of vibrations which is a multiple of the number producing some other overtones or undertones) can be a harmonic chord, which itself can be built up into a "tune". Each "tune" is suitable for the treatment of a specific symptom or disease. Lung diseases such as COPD, Asthma, Cystic Fibrosis and others can be treated in this way. Each disease has its own protocol of FPPs, which has been developed in relation to the effect on the tissues in question. For example, in order to clear Cystic Fibrosis mucus, a pressure impulse of particular pressure p1 and amplitude a1 at a certain frequency ω1 impinging upon the viscous mucus characteristic of CF has the effect of lowering its viscosity. Another pressure impulse of particular pressure p2, amplitude a2 and frequency ω2 has a direct effect of compressing the lung tissue momentarily, and a further particular pressure impulse of pressure p3 (which may be negative) amplitude a3 and frequency ω3, releases the tissue resiliently, thereby "flinging" the now less viscous mucus off the tissue wall, and unblocking it. A further example of the effects of the device would be frequencies directed to stimulating ciliary movement, assisting in expulsion of excess mucous, and others. The particular frequencies of the supplied FPPs, also influence the effect of the treatment. Likewise, the abovementioned amplitude-modulated FPPs (FIG. 1, 140), influence the result.

It is within provision of the invention that the device be provided with means for sensing the inhalation and exhalation stages of the subject's respiratory cycle. In this way, the device can provide a different sequence of FPPs on inhalation vs. exhalation. It is further within provision of the invention that different patient conditions be treated by different protocols, each of which may have one set of sequences of FPPs for use during inhalation, another set of sequences used during exhalation, and possibly a third set of sequences used during the intervals between inhalation and exhalation.

Devices for sensing of inhalation vs. exhalation will be well known to those skilled in the art, for example comprising pressure sensors, CO2 sensors, NO sensors, and others.

It is within provision of the invention to provide improvement in cardiac output, decrease in arterial resistance, decrease in capillary resistance, and increase in vascular elasticity by means of the vibrations and pressure variations induced by the device.

It is herein acknowledged that in some embodiments of the present invention, the protocols comprise not only the aforementioned sequences of FPPs, but also means and methods are provided to contemporaneously or simultaneously deliver streams of air with predetermined oscillating frequency into the patients airway, which persist for periods of time throughout or partially throughout the FPP sequences that are being delivered. Such airstreams can be likened to the drone of a Scottish bagpipe which produces a continuous stream of vibrating air at a predetermined frequency, whilst the chanter of the bagpipe produces the tune or melody. Certain particular predetermined oscillating frequencies of the aforementioned persistent streams of air are useful in stimulating NO production in certain tissues, promoting gas exchange and other therapeutically useful effects. Thus, some of the protocols of the invention will include the delivery of these drone-like vibrating airstreams in parallel to the predetermined sequences of FPPs.

The protocols exert their effects at the body organ level (e.g., lungs), the tissue level (e.g., bronchial smooth muscle relaxation, gas exchange at the alveolar membrane level), the cellular level (e.g., stimulation of epithelial NO production at the cellular level), the nervous system, parasympathetic nervous system, sympathetic nervous system, and others. There are several interrelated modes of interaction between the FPPs, including the setting up of resonating frequencies and harmonics with the natural resonances of different tissues.

The closest prior art relates to the supply of air impulses to the airway of patients, wherein the patient determines the frequency according to the level of comfort perceived by the patient. There is no teaching in the prior art of any preferred protocol for sequenced FPPs to alleviate any particular medical condition. An important facet of the invention is that means and methods are provided to design and implement any protocol for disease, based on sequences of FPPs. This is done by accumulating data from subjects provided with appropriate physiological sensors. In some embodiments the data will be fed back to fine tune the designed protocol. Protocols of the invention include particular frequencies and multiple harmonics or overtones thereof and are envisaged to cover the whole of relevant frequencies. Mechanical resonance is the tendency of a mechanical system to absorb more energy when the frequency of its oscillations matches the system's natural frequency of vibration (its resonance frequency or resonant frequency) than it does at other frequencies. It is herein acknowledged that some of the protocols of the present invention provide FPPs at the natural frequency of target tissues in the patient to facilitate the therapeutic effects of the treatment protocols.

It is within provision of the invention to provide effects currently achieved by conventional medicines, such as increased cardiac output, decreased arterial resistance, decreased capillary resistance, increase in vascular elasticity, and the like, increase/decrease in sympathetic/parasympathetic response, and the like.

It is within provision of the invention that clinical improvement can be attained during and/or after use of the device in a number of diseases and syndromes. The following is a partial list of such illnesses in which it is envisaged that the device may be of service:
Diseases:
Lung Diseases:
Obstructive Lung Diseases:
COPD
Asthma
Bronchitis
Restrictive Lung Diseases (e.g., asbestosis, radiation fibrosis, ARDS)
Cystic Fibrosis
Upper Respiratory Tract Infection:
Sinusitis
Pharyngitis
Laryngitis
Otitis Media
Lower Respiratory Tract Infections:
Pneumonia
Lung tumors
CardioVascular Diseases
Coronary heart disease
Cardiomyopathy (CM), e.g.:
Hypertrophic CM
Dilated CM
Hypertensive CM
Congestive Heart Failure
Inflammatory Heart Disease:
Endocarditis
Myocarditis
Cardiac Arrhythmias, e.g.:
Atrial fibrillation
Atrial flutter
Supraventricular Tachycardia
A-V blocks
Systemic Hypertension
Pulmonary hypertension
Atherosclerosis
Atherosclerosis of the Carotid arteries
Sleep apnea
Fibromyalgia It is further within provision of the invention that a number of biological responses can be attained through use of the device. The following is a partial list of such effects.
Biological Effects:
Smooth muscle relaxation
Pain blocking
Nitric Oxide release
Angiogenesis
Shear forces exerted on fibroblasts facilitate tissue regeneration
Relief of dyspnea (neural effect?)
Blood circulation
Improved perfusion through diseased capillaries
Improved alveolar gas exchange
Sympathetic function, Parasympathetic function, Autonomic balance
General influence on the nerves system and function
Change the chemical balance
Improvement of poorly functioning natural processes
Clinical Function Improvement Scales and Measurements It will be apparent to a person skilled in the art that the FPP protocols of the present invention and the means and methods of providing them will have a bearing on the wellness, i.e., the mental health, physical health and quality of life of the patient, as measured by various methods. Some of these methods are described below, in an exemplary manner, and a person skilled in the art may apply other measurements and criteria, all of which fall within the scope of the current invention.

There are various methods for measuring wellness or quality of life in patients, including the six minute walk test (6 MWT)

It is an aspect of the invention to provide an appropriate fluid pressure pulse (FPP) protocol useful for improving patient results as measured by the 6 MWT.

It is envisaged herein that the means and methods provided by the present invention, when applied to a patient in need, will provide a substantial improvement in results as measured by the 6 MWT.

Another test whose parameters will improve after application of the means and methods of the invention herein disclosed to a patient in need, is the incremental shuttle walking test (ISWT) which was developed to simulate a cardiopulmonary exercise test using a field walking test.

It is an aspect of the invention to provide an appropriate fluid pressure pulse (FPP) protocol useful for improving patient results as measured by the ISWT.

Lung Plethysmography Test

Another test whose parameters may improve after application of the means and methods of the invention herein disclosed to a patient in need is Lung plethysmography. This is a test used to measure how much air can be held in the patients lungs.

It is an aspect of the invention to provide an appropriate fluid pressure pulse (FPP) protocol useful for improving patient results as measured by Lung plethysmography.

Diffusion Capacity Test

Lung diffusion capacity testing (such as by the DLCO test) looks at how well gases are passing from the air sacs of the lungs into the blood, to determine whether the lung is sending enough oxygen into the blood. The test is used to diagnose certain lung diseases. It may also be used to see how gases move from the lungs into the bloodstream.

Abnormal results usually mean that gases do not move normally across the lung tissues into the blood vessels of the lung. This may be due to lung diseases such as: Emphysema, Interstitial fibrosis, Pulmonary hypertension, Sarcoidosis and others.

It is an aspect of the invention to provide an appropriate fluid pressure pulse (FPP) protocol useful for improving patient results as measured by a Lung Diffusion test or DLCO.

The Karnofsky scale is recognized by members of the medical community and persons skilled in the art as an objective standard by which a patient's quality of life can be assessed during the course of a treatment (see below)

The Karnofsky performance scale (KPS) is widely used as a screening criteria for clinical trial entry. It is a scale with 10 points ranging from completely healthy (100) to death (0). Key landmarks include ability to work, and being bed bound Karnofsky Scale
100 Asymptomatic, normal Function
80-90 Symptomatic, fully ambulatory
60-70 Symptomatic, in bed<50% of day
40-50 Symptomatic, in bed>50% of day
20-30 Bedridden
0 Death It is an aspect of the invention to provide an appropriate fluid pressure pulse (FPP) protocol useful for improving patient results as measured by the Karnofsky scale.

It is an aspect of the invention to provide an appropriate fluid pressure pulse (FPP) protocol useful for improving a patient's quality of life wherein the improvement in the patient's quality of life is measured by an increase in the patient's score of at least about 10 points on the Karnofsky scale compared to the patient's score prior to treatment.

It is an aspect of the invention to provide an appropriate fluid pressure pulse (FPP) protocol useful for improving a patient's quality of life wherein the improvement in the patient's quality of life is measured by an increase in the patient's score of at least about 20 points on the Karnofsky scale compared to the patient's score prior to treatment.

It is an aspect of the invention to provide an appropriate fluid pressure pulse (FPP) protocol useful for improving a patient's quality of life wherein the improvement in the patient's quality of life is measured by an improvement in the patient's symptoms as defined by the Karnofsky score selected from a group comprising of Bedridden to Symptomatic in bed >50% of day, Symptomatic, in bed >50% of day to Symptomatic, in bed <50% of day, or Symptomatic, in bed <50% of day to Symptomatic, fully ambulatory, or Symptomatic, fully ambulatory to Asymptomatic, normal Function.

Figure 6:
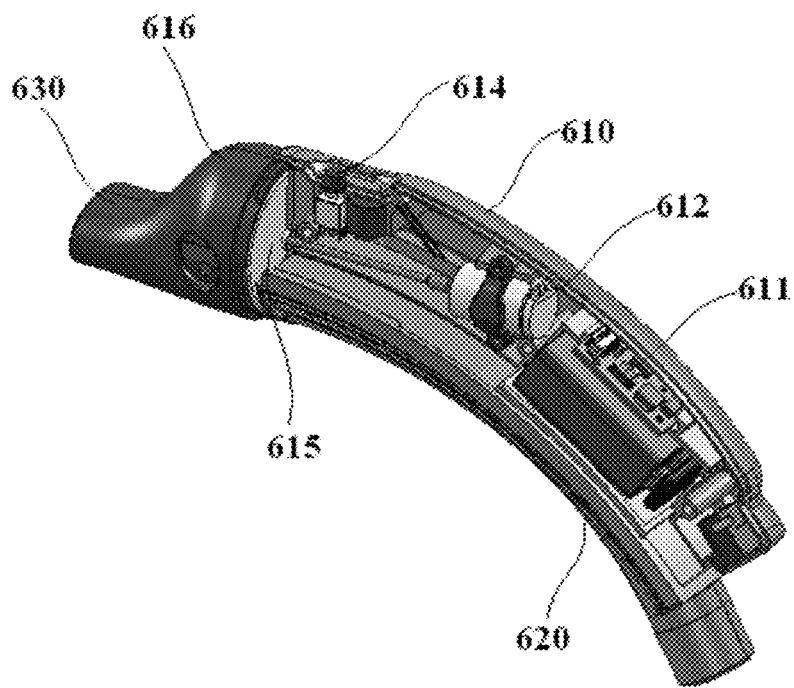
FIG. 6 is a schematic view of Pulshaler.

FIG. 6 herein illustrates and discloses an exemplary preferred device embodiment of the present invention which is useful for providing a protocol of Fluid Pressure Pulses (FPP) useful for improving a patients quality of life. The protocol provided by the exemplary device comprises predetermined sequences of predetermined FPPs.

The device in FIG. 6 provides the protocol to the airway of said patient, such that the protocol is contemporaneously administered to said patients inspirations and expirations, and in such a manner that the sequences of applied FPPs are independent from the patient's natural rates of inspiration and exhalation. Moreover, embodiments of the device are provided for administrating protocols additionally comprising at least one persistent or semi persistent stream of air of predetermined oscillating frequency administered in parallel with the sequences of applied FPPs.

The device in FIG. 6 which we define herein as a Pulsehaler, comprises a cassette 610, containing mechanical, control and electrical components, mounted on top of a conveniently shaped air tube 620, and a mouthpiece 630. The cassette 610 itself contains a computerized protocols controller 611, a motor, 612, an on/off switch 614, and a spinning disc 615 powered by the motor. The spinning disc 615 (provided with cutouts, slots or spaces) is arranged in such a way as to occlude the airstream in a predetermined manner according to the programme provided by the computerized protocols controller. In this way, the FPPs are produced. Changing discs, changing protocols or both, enable any manner of predetermined FPPs protocol deliverable by this device. The mouthpiece is provided with a release valve 616 for release of excess pressure during operation. It is of course envisaged that some embodiments of the device will be provided with an additional air tube, convenient for the delivery of the above mentioned drone-like vibrating airstreams in parallel to the predetermined sequences of FPPs, which are a feature of some of the protocols provided by this invention. It is yet further envisaged that some embodiments of the invention will be provided with a full or partial facemask, for delivery of the protocols. It is further herein acknowledged that, in some embodiments of the present invention, means and methods are provided for production and propagation of the drone-like vibrating airstreams by vibrating the spinning discs or the stationary discs accordingly, in order to provide the desired effect.

It is within provision of the invention that further means for changing the pressure waveform be employed, including but not limited to use of piezoelectric elements, sonic elements such as speakers or buzzers, pistons, pneumatic actuators, vibrators, and the like.

It is herein acknowledged that in some embodiments of the invention, one regulator or controller may control several different modes. Examples of modes include individual frequency, pressure amplitude, volume and duration.

Figure 7A:
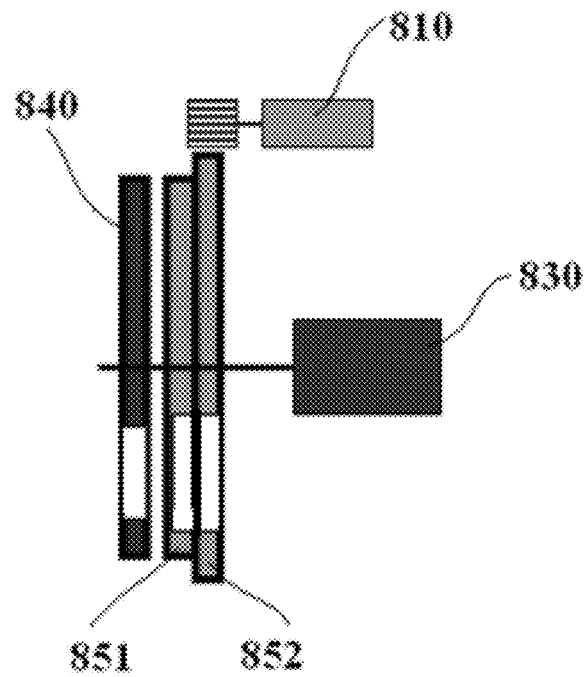
FIGS. 7a and 7b are schematic views of a disc arrangement.
Figure 7B:
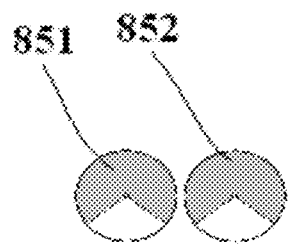
Figures 8A, 8B:
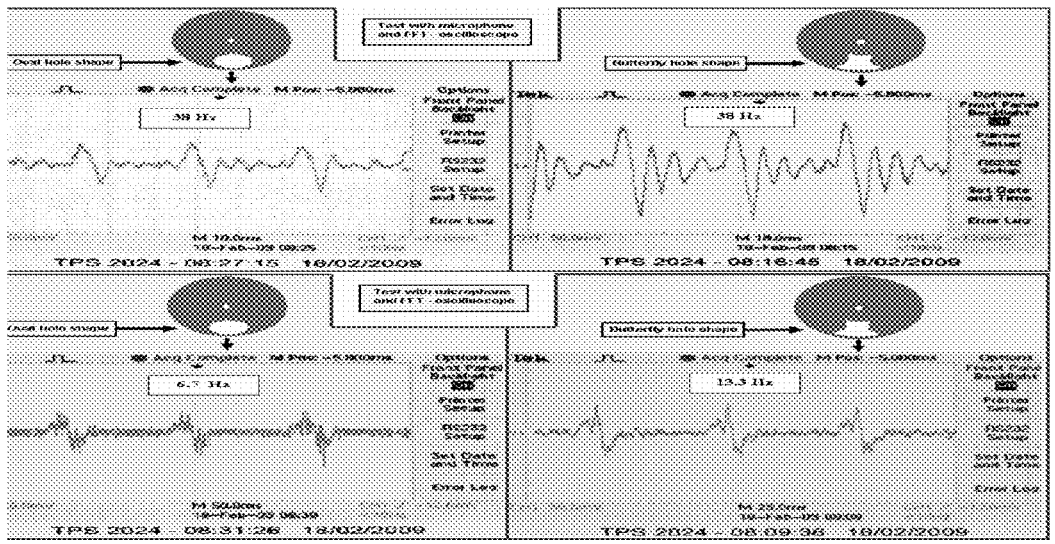
FIGS. 8a-8d present experimental graphs of pressure profiles created by rotating discs.
Figures 8C, 8D:
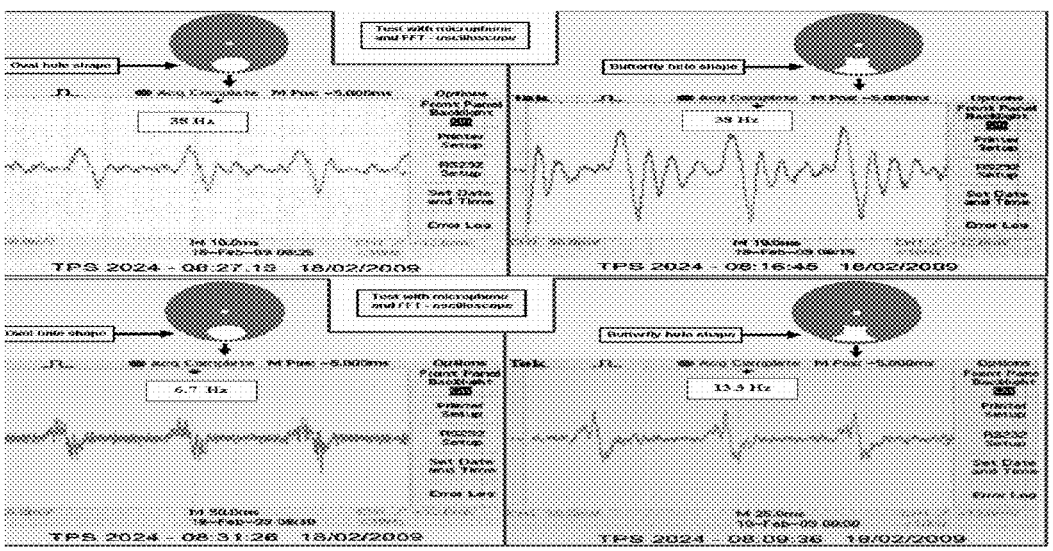

Some embodiments of the invention are provided with a plurality of rotating discs and stationary discs, which define the characteristics of the provided FPP protocol. Such an embodiment is schematically illustrated in FIGS. 7a and 7b for exemplary purposes.

A programmable motor 810 is provided for positioning of the stationary discs 851 and 852 relative to each other. The rotating discs 840 with various apertures, are spun around at predetermined revolutions by the rotating motor 830, and interrupt, or occlude, the fluid or air which is blown through the device by the fan or blower (not shown). The stationary discs 851 and 852 positioned against each other provide an entrainment for the air flow. The characteristics of the FPPs are thus easily provided and varied in a predetermined manner, according to the patients needs and the physiological measurements picked up by the sensors and fed back to the system controller (for example, the computerised protocols controller 611 of the exemplary Pulsehaler device shown in FIG. 6).

Reference is now made to FIGS. 8a-8d which depicts schematically the results of a standard oscilloscope experiment wherein the effects of different stationary disc configurations on the FPPs produced in a protocol are shown; discs with the "butterfly" cutout 900a produce, a characteristic FPP at 38 Hz, with a high pressure peak diminishing over time in characteristic fractions. At the same frequency of 38 Hz, use of a stationary disc with an oval hole 900b produces an FPP of a different pressure characteristic, with a different rising and falling profiles as illustrated in FIGS. 2,3. Thus a vast variety of FPPs can be administered in a predetermined manner, as required by the treatment, by means of different cutout shapes, disc turning speeds, and pressure levels.

Reference is further made to FIGS. 8a-8d which depicts schematically the results of a standard oscilloscope experiment wherein the effect of different stationary disc configurations on the FPPs produced in a protocol are shown; 9C shows that discs with the "butterfly" cutout produce, at 13.3 Hz, a characteristic FPP with a high pressure peak diminishing over time in characteristic fractions, but very different from the high pressure profile seen at 38 Hz, when the same butterfly disc is used as in 900a. Furthermore, at the same frequency of 6.7 Hz, use of a stationary disc with an oval hole 900d produces an FPP of a different pressure characteristic than that produced by the same disc at a frequency of 38 Hz, as seen in FIG. 9B. Thus a vast variety of FPPs can be administered in a predetermined manner, as required by the treatment, by varying frequency, disc hole shape and size, amplitude and pressure. Some embodiments of the present invention have been here above described, but it is envisaged that a person skilled in the art, will doubtlessly be able to construct and implement convenient variants based on these exemplary descriptions of both devices for implementing protocols and the protocols themselves.

A further discussion of the protocols at the core of the present invention follows:

The protocols disclosed herein are especially directed towards treating pulmonary related diseases such as COPD, CF, Asthma and others. Other aspects of the invention are directed towards critical medicine and respiratory support.

Pulmonary disorders have some disease elements in common, and some disease elements unique or specific to each disorder. The present invention discloses and provides protocols for treating and modifying these elements in one treatment. It is an important aspect of the present invention to provide specific FPP protocols which can change according to requirements at different stages of the disease progression, remission or improvement, and are suited to the needs of each individual patient during the course of treatment or therapy.

The following are non limiting examples of diseases or conditions which can be alleviated by use of the present invention Asthma The FPP protocol is applied to provide an effect on the complete respiratory system, With emphasis on relaxation of smooth muscle tissue and opening of the bronchus, clearing and absorbing mucus from the bronchus, lowering of residual volume and increasing of functional volume. Therapeutic effects of the specific FPP protocol are also directed towards increase of blood circulation and pulmonary gas exchange.

Cystic Fibrosis

In contrast to the FPP protocols for asthma therapy, the FPP protocols directed towards cystic fibrosis therapy provide the appropriate FPPs necessary for reduction of the viscosity of the mucus characteristically produced in CF patients, and the concomitant release of the mucus from the lungs and airway.

COPD

For COPD, the FPP protocols are designed and directed towards improving respiratory and in some cases cardio vascular functions. The protocols are designed to elicit improvement in multiple factors including but not limited to one or more of the following: restoring the functionality of previously non functioning or under-functioning regions of the lungs, reducing pulmonary blood pressure, reducing the right ventricular pressure of the patients heart, increased clearance of mucus, reduction of overall secretions, and increasing overall oxygen absorption.

The above mentioned examples are meant to illustrate in a non limiting manner the number of specific FPP protocols which are envisaged and provided by the specific invention.

The combination of the protocols provided and their generation by the above mentioned especially provided shutter-like discs or similar components constitute a core aspect of the invention.

Congestive Heart Failure (CHF)

Heart failure is the pathophysiologic state in which the heart, via an abnormality of cardiac function (detectable or not), fails to pump blood at a rate commensurate with the requirements of the metabolizing tissues and/or pumps only from an abnormally elevated diastolic filling pressure.

Congestive Heart Failure is an illness in which the pumping action of the heart becomes less and less powerful. That is, the heart does not pump blood as well as it should. When this happens, blood does not move efficiently through the circulatory system and starts to back up, increasing the pressure in the blood vessels and forcing fluid from the blood vessels into body tissues.

Pulmonary Oedema

When the left side of the heart starts to fail, fluid collects in the lungs (pulmonary edema). This extra fluid in the lungs (congestion) makes it more difficult for the airways to expand as the subject inhales. Breathing becomes more difficult, and shortness of breath may be felt, particularly with activity or lying down.

Some embodiments of the invention provide FPP protocols and means of producing and applying them are designed and directed towards improving respiratory and in some cases cardio vascular functions for CHF and for Pulmonary Oedema patients. The protocols are designed to elicit improvement in multiple factors including but not limited to one or more of the following: restoring the functionality of previously non functioning or under-functioning regions of the lungs, reducing pulmonary blood pressure, reducing the right ventricular pressure of the patients heart, reducing the left ventricular pressure of the patients heart, increased clearance of mucus, reduction of overall secretions, and increasing overall oxygen absorption.

The above mentioned examples are meant to illustrate in a non limiting manner the number of specific FPP protocols which are envisaged and provided by the specific invention.

The combination of the protocols provided and their generation by the above mentioned especially provided shutter-like discs or similar components constitute a core aspect of the invention.

Protocols

Examples of specific protocols provided by the invention are presented in Table 1.

TABLE 1

Therapeutic Protocols for Asthma, COPD and CF

| Disease | Step number | Frequency, Hz | Rpm of rotating disc | Duration, min | Remarks |
|---|---|---|---|---|---|
| Asthma | 1 | 60.0 ± 7.0 | 3600 ± 360 | 1.0 ± 0.1 | — |
|  | 2 | 8.0 ± 0.9 | 480 ± 48 | 1.5 ± 0.15 | — |
|  | 3 | 5.0 ± 0.6 | 300 ± 30 | 1.5 ± 0.15 | — |
|  | 4 | 25.0 ± 3.0 | 1500 ± 150 | 2.5 ± 0.25 | — |
|  | 5 | 0 | 0 | 1.0 ± 0.1 | Rest |
|  | 6 | 13.0 ± 7.0 | 780 ± 78 | 1.5 ± 0.15 | — |
|  | 7 | 7.0 ± 7.0 | 720 ± 72 | 1.5 ± 0.15 | — |
|  | 8 | 0 | 0 | 1.0 ± 0.1 | Rest |
|  | 9 | 34.0 ± 7.0 | 2040 ± 204 | 2.5 ± 0.25 | — |
|  | 10 | 19.0 ± 7.0 | 1140 ± 114 | 3.0 ± 0.3 | — |
|  | Total |  |  | 17 | — |
| COPD | 1 | 60.0 ± 7.0 | 3600 ± 360 | 0.5 ± 0.05 | — |
|  | 2 | 5.0 ± 0.6 | 300 ± 30 | 3.0 ± 0.3 | — |
|  | 3 | 7.0 ± 7.0 | 438 ± 42 | 2.0 ± 0.2 | — |
|  | 4 | 0 | 0 | 1.0 ± 0.1 | Rest |
|  | 5 | 13.0 ± 7.0 | 780 ± 78 | 3.0 ± 0.3 | — |
|  | 6 | 34.0 ± 7.0 | 2040 ± 204 | 2.0 ± 0.2 | — |
|  | 7 | 0 | 0 | 1.0 ± 0.1 | Rest |
|  | 8 | 5.0 ± 0.6 | 300 ± 30 | 2.0 ± 0.2 | — |
|  | 9 | 13.0 ± 7.0 | 780 ± 78 | 2.0 ± 0.2 | — |
|  | 10 | 25.0 ± 3.0 | 1500 ± 150 | 2.0 ± 0.2 | — |
|  | Total |  |  | 18.5 | — |
| CF | 1 | 60.0 ± 7.0 | 3600 ± 360 | 0.5 ± 0.5 | — |
|  | 2 | 10.0 ± 7.0 | 600 ± 60 | 2.0 ± 0.2 | — |
|  | 3 | 5.0 ± 0.6 | 300 ± 30 | 3.0 ± 0.3 | — |
|  | 4 | 0 | 0 | 1.0 ± 0.1 | Rest |
|  | 5 | 7.0 ± 7.0 | 438 ± 42 | 2.0 ± 0.2 | — |
|  | 6 | 13.0 ± 7.0 | 780 ± 78 | 2.0 ± 0.2 | — |
|  | 7 | 0 | 0 | 1.0 ± 0.1 | Rest |

TABLE 1-continued

Therapeutic Protocols for Asthma, COPD and CF

| Disease | Step number | Frequency, Hz | Rpm of rotating disc | Duration, min | Remarks |
|---|---|---|---|---|---|
|  | 8 | 5.0 ± 0.6 | 300 ± 30 | 3.0 ± 0.3 | — |
|  | 9 | 34.0 ± 7.0 | 2040 ± 204 | 2.0 ± 0.2 | — |
|  | 10 | 34.0 ± 7.0 | 1080 ± 108 | 3.0 ± 0.3 | — |
|  | Total |  |  | 19.5 | — |

Protocols for Inspiration and Expiration:

In some embodiments of the present invention, a sensor at an opening of the device detects inspiration and expiration and accordingly signals the controller. The controller selects, alters or changes the FPP protocol that will be provided to the patient according to the predetermined programme.

If, for example, the 34 Hz frequency widens the bronchioles during inspiration, and 5 Hz during expiration facilitates expectoration, the appropriate frequencies will be provided. As a result, the bronchioles are widened and expectoration is increased.

If, for example, FPPs provided at a frequency of 40 Hz improve blood circulation during inspiration, and gas exchange is improved during expiration upon application of 8 Hz FPPs, then those frequencies will be automatically selected. Such a therapeutic treatment will be beneficial, because one will have, for example, lowered pulmonary pressure and improved oxygenation.

Protocols for Respiration, Changes in Pressure and Capacity

It is an embodiment of the present invention to provide and disclose sensors and methods of using them to detect gases exhaled during respiration which then transfer signals to the controller. The controller can alter and change the frequency or frequencies of the provided FPPs of the specific protocol or select a protocol at the beginning of treatment. The FPP supply to the patient's airway can be generated by Turbine-like devices, CPAP-like devices, BILEVEL like devices, breathing and respiration devices, assisted breathing and similar for inspiration and expiration. Similarly, it is envisaged that the FPPs of the applied protocols can be of positive pressure, negative pressure, or a combination of both. Means and methods of providing resistance and perturbations to the natural breathing patterns of an individual patient are herein provided with protocols. Means and methods of selecting and generating such FPP protocols characterized by supplying FPPs of various frequencies, pressures and other characteristics, tailored according to the patients condition at the beginning of the therapy and during it's progress are provided. Thus the invention herein disclosed provides a non limited solution to pulmonary, respiration related and critical care patients.

Table 2 is a more detailed example of selected protocols for Asthma treatment, COPD or CF. It should be noted that for each condition, a series of FPPs are administered of predetermined Hz and duration. The RPM in the table refers to the revolutions of the revolving disc of exemplary embodiments of the invention, but any convenient means of producing the FPP's can be employed and remain within the scope of the invention. It should further be noted that each protocol has a predetermined Hz and duration of the FPP application which is selected because they have been found to beneficially effect certain physiological characteristics such as blood circulation, mucus transport, gas exchange, Functional residual capacity and relaxation smooth muscles, mucus transport in the upper bronchial region, blood circulation, Functional/residual capacity.

TABLE 2

| Asthma | Hz | RPM | duration (minutes) | |
|---|---|---|---|---|
| 1 | 40* | 2400 | 1 | |
| 2 |  | 480 | 1.5 | |
| 3 |  | 300 | 1.5 | |
| 4 | 25*** | 1500 | 2.5 | |
| 5 | 0 | 0 | 1 | Rest |
| 6 |  | 600 | 2 | |
| 7 | 13*** | 780 | 1.5 | |
| 8 | 16*** | 960 | 2 | |
| 9 |  | 420 | 1.5 | |
| 10 | 0 | 0 | 1 | Rest |
| 11 | 34*** | 2040 | 2.5 | |
| 12 | 19*** | 1140 | 3 | |
| total |  |  | 21 | |

| COPD Step | Hz | RPM | duration (minutes) | |
|---|---|---|---|---|
| 1 | 40* | 2400 | 1 | |
| 2 |  | 300 | 2 | |
| 3 |  | 420 | 2 | |
| 4 |  | 438 | 2 | |
| 5 | 0 | 0 | 1 | Rest |
| 6 | 19*** | 1140 | 2 | |
| 7 |  | 480 | 2 | |
| 8 | 25*** | 1500 | 2 | |
| 9 | 0 | 0 | 1 | Rest |
| 10 |  | 600 | 2 | |
| 11 | 34*** | 2040 | 2 | |
| 12 | 16*** | 960 | 2 | |
| 13 | 50* | 3000 | 1 | |
| total |  |  | 22 | |

| CF | Hz | RPM | duration (minutes) | |
|---|---|---|---|---|
| 1 | 40* | 2400 | 0.5 | |
| 2 |  | 600 | 2 | |
| 3 |  | 240 | 1.5 | |
| 4 |  | 300 | 2 | |
| 5 |  | 480 | 1.5 | |
| 6 | 0 | 0 | 1 | Rest |
| 7 |  | 438 | 1.5 | |
| 8 |  | 360 | 1 | |
| 9 | 13*** | 780 | 2 | |
| 10 | 0 | 0 | 1 | Rest |
| 11 |  | 300 | 2 | |
| 12 | 34*** | 2040 | 2 | |
| 13 | 19*** | 1080 | 3 | |
| total |  |  | 21 | |

■ blood circulation*

▨ mucus transport, gas exchange, Functional residual capacity**

▦ relaxation smooth muscles, mucus transport upper bronchial, blood circulation, Functional/residual capacity***

□ Rest

| minute |  | % |
|---|---|---|
| 1 | * | 4.8 |
| 6.5 | ** | 31.0 |
| 11.5 | *** | 54.8 |
| 2 | Rest | 9.5 |
| 21 | total | 100 |

| minute |  | % |
|---|---|---|
| 2 | * | 9.1 |
| 10 | ** | 45.5 |
| 8 | *** | 36.4 |
| 2 | Rest | 9.1 |
| 21 | total | 100 |

| minute |  | % |
|---|---|---|
| 0.5 | * | 2.4 |
| 11.5 | ** | 54.8 |
| 7 | *** | 33.3 |
| 2 | Rest | 9.5 |
| 21 | total | 100 |

The asterisks (*, , *) in table 2 designate the physiological characteristics aforementioned, yet many other characteristics are envisaged as aspects of the current invention, which will be applied by means and methods of the present invention.

Examples for 16 breathing cycles (inhalation/exhalation) per minute total 8 minutes

| minute | 1 | | 2 | | 3 | | 4 | | 5 | | 6 | | 7 | | 8 | |
|---|---|---|---|---|---|---|---|---|---|---|---|---|---|---|---|---|
|  | 1 minute | | 1 minute | | 1 minute | | 1 minute | | 1 minute | | 1 minute | | 1 minute | | 1 minute | |
| cycle |  | Hz |  | Hz |  | Hz |  | Hz |  | Hz |  | Hz |  | Hz |  | Hz |
| 1 | in | 34 | in | 19 | in | 16 | in | 16 | in | 40 | in | 25 | in | 16 | in | 16 |
|  | ex | 5 | ex | 7.3 | ex | 5 | ex | 5 | ex | 8 | ex | 5 | ex | 5 | ex | 5 |
| 2 | in | 34 | in | 19 | in | 16 | in | 16 | in | 40 | in | 25 | in | 16 | in | 16 |
|  | ex | 5 | ex | 7.3 | ex | 5 | ex | 5 | ex | 8 | ex | 5 | ex | 5 | ex | 5 |
| 3 | in | 34 | in | 19 | in | 16 | in | 16 | in | 40 | in | 25 | in | 16 | in | 16 |
|  | ex | 5 | ex | 7.3 | ex | 5 | ex | 5 | ex | 8 | ex | 5 | ex | 5 | ex | 5 |

Examples for 16 breathing cycles (inhalation/exhalation) per minute total 8 minutes

| | | | | | | | | | | | | | | | | |
|---|---|---|---|---|---|---|---|---|---|---|---|---|---|---|---|---|
| 4 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 5 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 6 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 7 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 8 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 9 | in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 10| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 11| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 12| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 13| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 14| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 15| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |
| 16| in | 34 | in | 19 | in | 16 | in | 16 | in | 40 | in | 25 | in | 16 | in | 16 |
|   | ex | 5  | ex | 7.3| ex | 5  | ex | 5  | ex | 8  | ex | 5  | ex | 5  | ex | 5  |

The above description has, in a non limited manner, described an Air Delivery Device (ADD) and protocols for the application of the aforementioned Fluid Pressure Pulses (FPPs) to the airways of patients in need. It is envisaged that a person skilled in the art will be able, by learning from the disclosure herein provided, to provide means and methods for treating a wide number of diseases, symptoms and conditions, itionally to COPD, Asthma and Cystic Fibrosis. Such diseases symptoms and conditions include: Sinustis, Nasal Congestion, Pneumonia, Emphysema, Interstitial fibrosis, Pulmonary hypertension or Sarcoidosis.

It is furthermore envisaged that the above mentioned ADD and protocols will be useful in improving a patient's condition as measured by parameters, indices and scales selected from the group consisting of mental and physical health, quality of life, lung function, drug uptake, heart function, cardio-vascular efficiency, pulmonary efficiency, lung volume, oxygen uptake, gas exchange, NO production, carbon monoxide diffusion or any combination thereof.

As further examples of possible protocols, we present the graphs of FIGS. 9-12. These figures represent pressure as a function of time. The mathematical representation of the pressure as a function of time may take the form of triangle waves, square waves, sine waves. and others, all possibly modulating one another. Thus for example possible pressure sequences include but are not limited to:

$$P(t) = A \sin^{-1}(\sin(\omega_1 t)) + B \times \theta(\sin(\omega_2 t)) + C$$

where $\theta(t)$ is the Heaviside step function, $$\theta(x) = \begin{cases} 1; & x \geq 0 \\ 0; & x < 0 \end{cases}$$

$$P(t) = A \sin^{-1}(\sin(\omega_1 t)) + B \times \theta(\sin(\omega_2 t)) + C$$

$$P(t) = A \sin^{-1}(\sin(\omega_1 T)) + B \sin^{-1}(\sin(\omega_2 t)) + C$$

and others as will be obvious to one skilled in the art. The constants A, B, C, $\omega_1$, and $\omega_2$ are chosen for instance such that 0.01 Hz $\leq \omega_1 \leq$ 1 Hz, 0.1 Hz $\leq \omega_2 \leq$ 10 Hz, 10 mmHg $\leq A \leq$ 250 mmHg, 10 mmHg $\leq B \leq$ 250 mmHg, and −250 mmHg $\leq C \leq$ 250 mmHg. Change high herz to 250 Hz It is within provision of the invention to provide enhancement of sporting performance and/or post-event recuperation. Since the device has been clinically demonstrated to cause dramatic improvements in e.g. 6 minute walk tests (see below), it is likely that improvements in blood oxygen levels and the like due to use of the device will provide similar improvements in the realm of sport and recreation.

It is within provision of the invention that the protocols used in operation of the device provide specific levels of pressure based on the expiratory resistance of the subject.

In the following section an analysis of the device and methods of the current invention is presented.

Experiment 1: The Effect of PulseHaler™ Cardiopulmonary Device on Cardiac Function and Peripheral Tissue Blood Gases (2009)

Abstract

PulseHaler™ Cardiopulmonary Device is a novel device developed for the treatment of cardiovascular, pulmonary and systemic conditions, by means of pulsating airflow administered through the patient's airway according to predefined protocols. In this study, the effect of a 22-minute treatment on cardiopulmonary functions was studied, by means of analyzing heart rate and heart rate variability, and measuring peripheral tissue O2 and CO2 levels. The results suggest that PulseHaler stimulates vagal activity, causing heart rate to decrease and heart rate variability to increase; and they further show that PulseHaler treatment affected blood gas levels, raising peripheral oxygenation and lowering the levels of peripheral tissue CO2.

Background

PulseHaler™ Cardiopulmonary Device is a novel device for treatment of cardiovascular and pulmonary diseases. Pulsehaler is based on novel technology, and it administers pulsating airflow through the patient's respiratory tract, according to pre-defined protocols.

PulseHaler™ is pre-programmed to deliver airflow at pre-defined frequencies, pressure amplitude, waveform and durations.

Reduced resting heart rate is a consequence of an increase in parasympathetic influence on the heart rhythm. Associated with this increase in cardiac vagal influence is an increase in respiratory related heart rate variability (HRV) with the heart rate accelerating during inspiration and slowing during expiration. This sinus arrhythmia is dependent on fluctuations in cardiac vagal excitability induced by two main mechanisms: 1) Baroreceptor discharge due to respiratory induced variation in stroke volume and blood pressure. 2) The magnitude of the $CO_2$ dependent central inspiratory inhibitory influence on cardiac vagal neurons.

Autonomic nervous control of heart rate can be determined by the measurement of HRV using variety of methods including:
1. RMSSD—root mean square of the difference between successive NN intervals (the time intervals between consecutive Normal beats, reflecting the underlying sinus rhythm). RMSSD is a time domain measure of HRV that is sensitive to short-term, high-frequency fluctuations and is a commonly used index in clinical cardiology. RMSSD statistic is more sensitive to vagal cardiac control and less to the sympathetic influence.
2. SDNN (standard deviation Normal to Normal) is another measure of HRV: it is the standard deviation of the Normal to Normal intervals measured in a given time period. SDNN is a prominent predictor and diagnostic tool for cardiovascular disease.
3. pNN50—percentage of adjacent NN intervals that differ by more than 50 ms
4. HF—frequency domain measures of the power concentrated at the respiratory frequency.

These measures of cardiac vagal activity have been found to be powerful and independent prognostic indicators. In patients with heart failure and myocardial infractions, as well as in the general population, reduced HRV is a marker of adverse prognosis. As a result of numerous studies it has been suggested that the association between cardiac vagal activity may directly and adversely influence the natural history of cardiac disease.

The physiological effect of vagal activity is to decrease cardiac work by reducing resting heart rate and contractility. The reduction in contractility combined with a reduction in heart rate results in a profound reduction in cardiac work and myocardial oxygen demand and may be advantageous in the context of coronary artery disease and left ventricular dysfunction. Stimulation of the vagus nerve inhibits sympathetic nerve activity via peripheral pre- and post-synaptic interactions (prolonged sympathetic over activity induce well recognized cytotoxic effects and apoptosis). Finally, cardiac vagal activity appears to reduce the hearts vulnerability to potentially lethal ventricular arrhythmia.

Objectives
1. Determine the effect of PulseHaler™ on Heart rate variability (HRV).
2. Determine the effect of of PulseHaler™ on tissue gases (O2, CO2).

Methods 42 years smoking male volunteer was subjected to PulseHaler treatment. Tissue, gases were determined at the back of the left hand near the thumb. ECG was recorded (Lead II) for half an hour before the treatment, during the treatment, and for half an hour after the treatment. HRV and ECG parameters were calculated from the ECG record. Baseline HRV was calculated from 5 min ECG strip 50 min before PulserHaler™ treatment, 22 min after PulseHaler™ treatment another set of HRV parameters were calculated from 5 min ECG strip.

Results
1. As can be seen from Table 3, 22 min after treatment with PulseHaler™ the heart rate decreased from 77.5 BPM at the base line level (50 min before treatment) to 63.4 BPM after treatment, an 18.4% decrease. SDNN increased after PulseHaler treatment by 64.4%. From Table 3 RMSSD increased after PulseHaler treatment by 250%. One can see that after PulseHaler treatment the pNN50 was also much higher compared to baseline values.

TABLE 3

HRV parameters as measured before and after PulseHaler treatment

| | Baseline | After PulseHaler treatment |
|---|---|---|
| Length of recording | 300 sec | 300 sec |
| Average heart rate | 77.5 | 63.4 |
| SDNN | 43.65 ms | 67.77 ms |
| RMSSD | 14.53 ms | 36.89 ms |
| $_T$pNN50 | 0.7% | 12.93% |
| Total power | 1772.18 ms$^2$ | 4013.13 ms$^2$ |
| VLF | 1112.7 ms$^2$ | 1671 ms$^2$ |
| LF | 588.43 ms$^2$ | 2019.55 ms$^2$ |
| | 89.22 nu | 86.22 nu |
| HF | 63.96 ms$^2$ | 294.06 ms$^2$ |
| | 9.699 nu | 12.55 nu |
| LF/HF | 9.19 | 6.86 |

HRV calculation in the frequency domain shows that HF (high frequency) peak is higher (nu) after the treatment and the LF peak is with no significant change. The LF/HF ratio that represents the sympathetic/parasympathetic balance is much lower after the treatment indicating higher vagal activity.

2. Shortly after treatment onset, the $O_2$ levels ascend from average 55 mmHg to 64 mmHg during the treatment. After the treatment $TCpO_2$ level continued to increase up to 85 mmHg 12 min after treatment. Concomitantly $TCpCO_2$ levels declined from baseline of 34 mmHg to 20.4 mmHg during the treatment and returned to 29 mmHg 12 min after the treatment. Generally, the arteriovenous circulation time of the hand is very short. Thus, early venous contamination occurs as shown by the low level of baseline $TCpO_2$ (55 mmHg).

3.

TABLE 4

Transcutaneous gas parameters on the back of the hand

| | TCpO$_2$ mmHG | TCpCO$_2$ mmHg |
|---|---|---|
| Base line | 55 | 34 |
| during treatment | 64 | 20.4 |
| 2 min after treatment | 70.3 | 21.8 |
| 4 min after treatment | 72.8 | 24.6 |
| 6 min after treatment | 77.2 | 26.2 |
| 8 min after treatment | 81.2 | 27.4 |
| 10 min after treatment | 84.4 | 29.5 |
| 12 min after treatment | 85 | 29 |

Conclusions

In this study, we show that a 22-minute treatment with PulseHaler elicits vagal activation and shifts the autonomic balance to the parasympathetic side. This is apparent from both the time-domain measurements, i.e., reduction of the heart rate and increase of the SDNN, RMSSD and pNN50; and from the frequency-domain calculations, i.e., LF, HF and the LF/HF ratio, which show an increase of heart rate variability.

Additionally we show an increase in peripheral tissue oxygenation and concomitant reduction in peripheral tissue CO2 levels. Interestingly, blood gases levels continued in the same trend after the treatment stopped, for at least 12 minutes, indicating better cardio-pulmonary function, which persists beyond the treatment period itself.

Figure 9A:
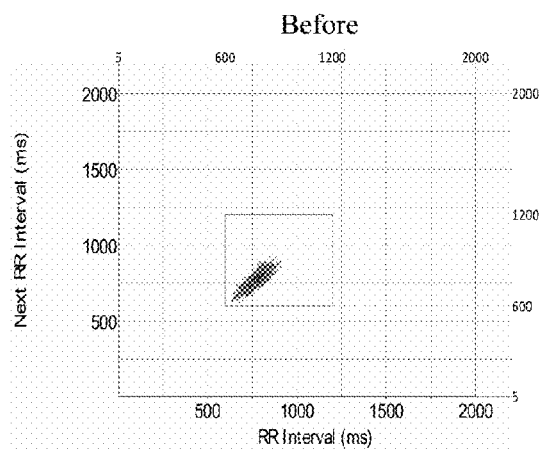
FIGS. 9a-9c present experimental RR/RR graphs.
Figure 9B:
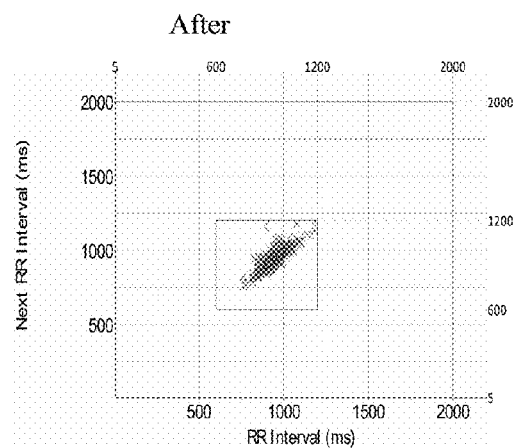
Figure 9C:
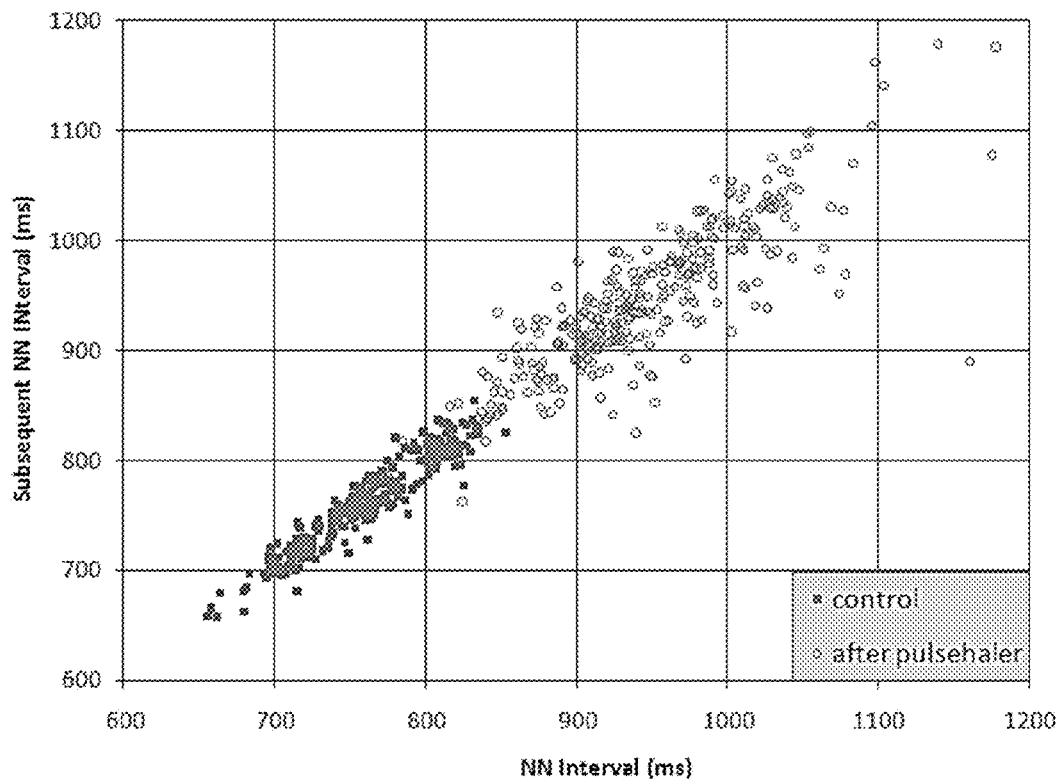
Figure 9D:
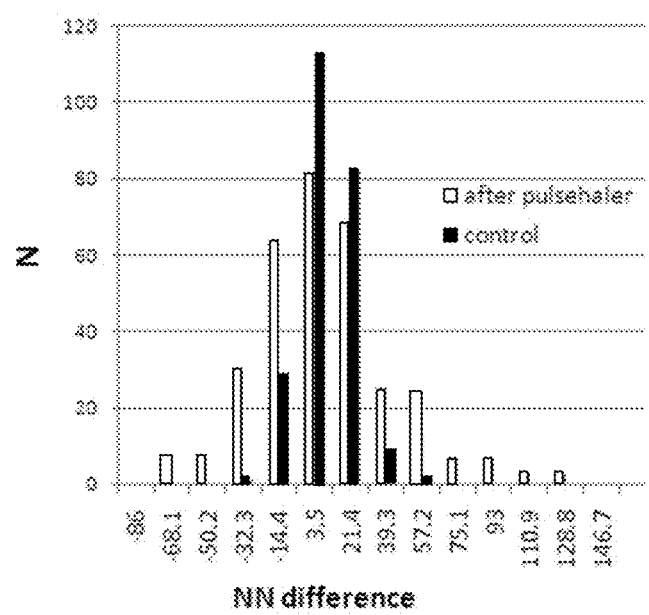
FIG. 9d presents a histogram of differences between successive N—N intervals.

The ECG recorded in the study is represented in the next RR/RR graphs of FIGS. 9a-9c, which shows plots of the RR on the x-axis vs. the subsequent RR on the y-axis. The graph on the right of FIG. 14a is the record before the treatment and the graph on the left is the record after PulseHaler™ treatment. The record on the right shows low RR variability while on the left (after PulseHaler™ treatment) higher heart variability but within the boundaries of normal RR intervals. FIG. 9c shows the same data but on shared axes, highlighting the differences between the datasets; the control is more tightly grouped and on average faster. FIG. 9d shows the differences between successive N—N intervals, presented as a histogram. As is clear from the figure, the spread of the control is much less than that of the post-treatment data.

Figure 10:
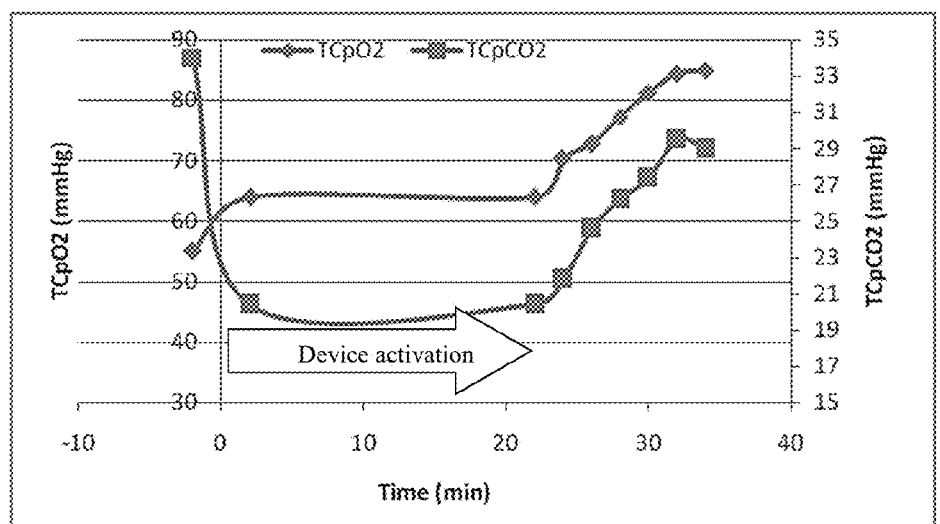
FIG. 10 presents graphs transcutaneous $O_2$ and $CO_2$.

FIG. 10 shows the transcutaneous O$_2$ and CO$_2$ measurement at the back of the hand. TCpO$_2$ levels increased during the treatment and afterwards reaching higher levels than the baseline. Concomitantly TCpCO$_2$ decreased during the treatment and ascend at the end of the treatment, but did not returned to baseline level after 12 min of record.

Experiment 2: An Example of Cardiopulmonary Combination Treatment for Patients with Heart Failure and COPD In this experiment the pulsehaler was used to treat patients suffering both from heart failure and COPD. The table below lists indicates the therapeutic protocols used.

TABLE 5

Therapeutic Protocol for cardiopulmonary system

| Step number | Main frequency Hz | Rpm of rotating disc | 1st Harmony Hz | 2nd Harmony Hz | 3rd Harmony Hz | Duration sec | Remarks |
|---|---|---|---|---|---|---|---|
| 1 | 39.0 ± 0.2 | 2340 | 78 | 117 | 156 | 55 | — |
| 2 | 13.5 ± 0.2 | 810 | 27 | 40.5 | 54 | 112 | — |
| 3 | 7.5 ± 0.2 | 450 | 15 | 22.5 | 30 | 106 | — |
| 4 | 4.7 ± 0.2 | 282 | 9.4 | 14.1 | 18.8 | 106 | — |
| 5 | Recovery | | | | | 30 | Rest |
| 6 | 19.0 ± 0.2 | 1140 | 38 | 57 | 75 | 81 | |
| 7 | 25.5 ± 0.2 | 1530 | 51 | 76.5 | 102 | 68 | — |
| 8 | 33.3 ± 0.2 | 1998 | 66.6 | 99.9 | 133.2 | 59 | — |
| 9 | 50.0 ± 0.2 | 3000 | 100 | 150 | 200 | 55 | — |
| 10 | Recovery | | | | | 30 | Rest |
| 11 | 6.5 ± 0.2 | 390 | 13 | 19.5 | 26 | 106 | — |
| 12 | 13.5 ± 0.2 | 810 | 27 | 40.5 | 54 | 112 | — |
| 13 | 33.3 ± 0.2 | 1998 | 66.6 | 99.9 | 133.2 | 106 | — |
| 14 | 4.7 ± 0.2 | 282 | 9.4 | 14.1 | 18.8 | 106 | |
| 15 | 19.0 ± 0.2 | 1140 | 38 | 57 | 16 | 81 | |
| 16 | Recovery | | | | | 30 | Rest |
| 17 | 51.0 ± 0.2 | 3060 | 102 | 153 | 204 | 55 | |
| 18 | 25.5 ± 0.2 | 1530 | 51 | 75.6 | 102 | 68 | |
| total | | | | | | 1366 | |

Examples from the protocol:

| | |
|---|---|
| Reduce the shortness of breath | |
| Reduce the mucus viscosity | |
| Increase the cough instinct | |
| Moving the Respiratory Cilia | |
| Changing parasympathetic/sympathetic balance | |
| Increase pulmonary gas exchange | |
| Increase nitric oxide production | |
| Increase the capillary function | |
| Relaxation the heart ventricles | |
| Enhance lungs\heart circulation | |
| Enhance coronary, heart muscles perfusion | |

In FIG. 17 the protocol is depicted in the form of a 3D bar chart. The x-axis corresponds to time, and the other axes to amplitude and frequency.

In FIG. 18 data is presented concerning the operation of the device and its various harmonics, with time on the x-axis.

In FIGS. 19-23 power spectra of the response to the device are shown.

Figure 11:
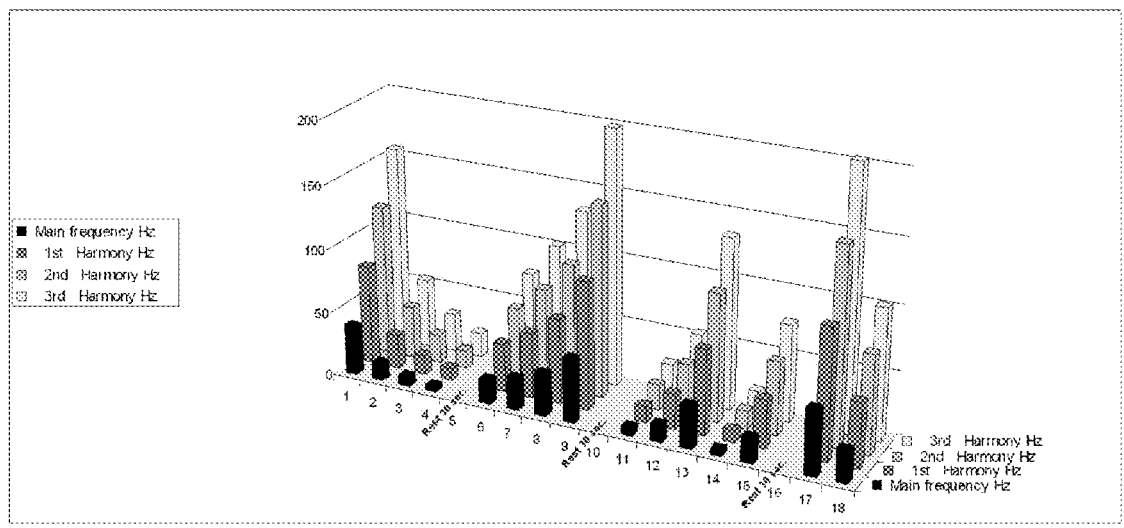
FIG. 11 presents a diagram of harmonic amplitudes.
Figure 12:
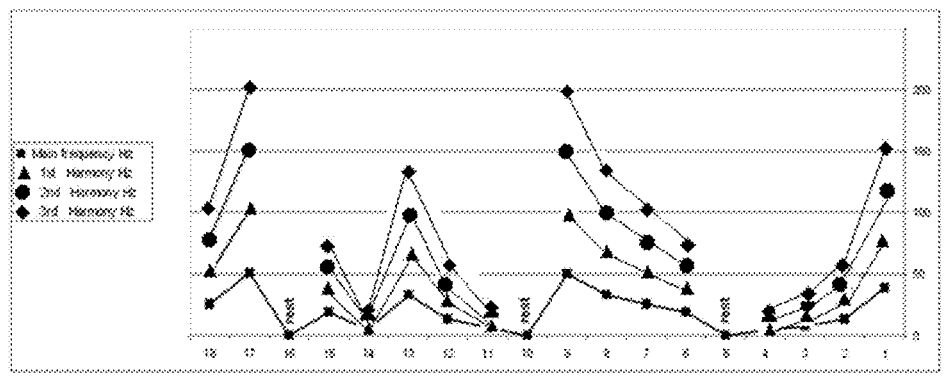
FIG. 12 present operation of the device and its various harmonics.

In FIG. 11, the protocol is depicted in the form of a 3D bar chart. The x-axis corresponds to time, and the other axes to amplitude and frequency.

In FIG. 2 data is presented concerning the operation of the device and its various harmonics, with time on the x-axis.

Figure 13:
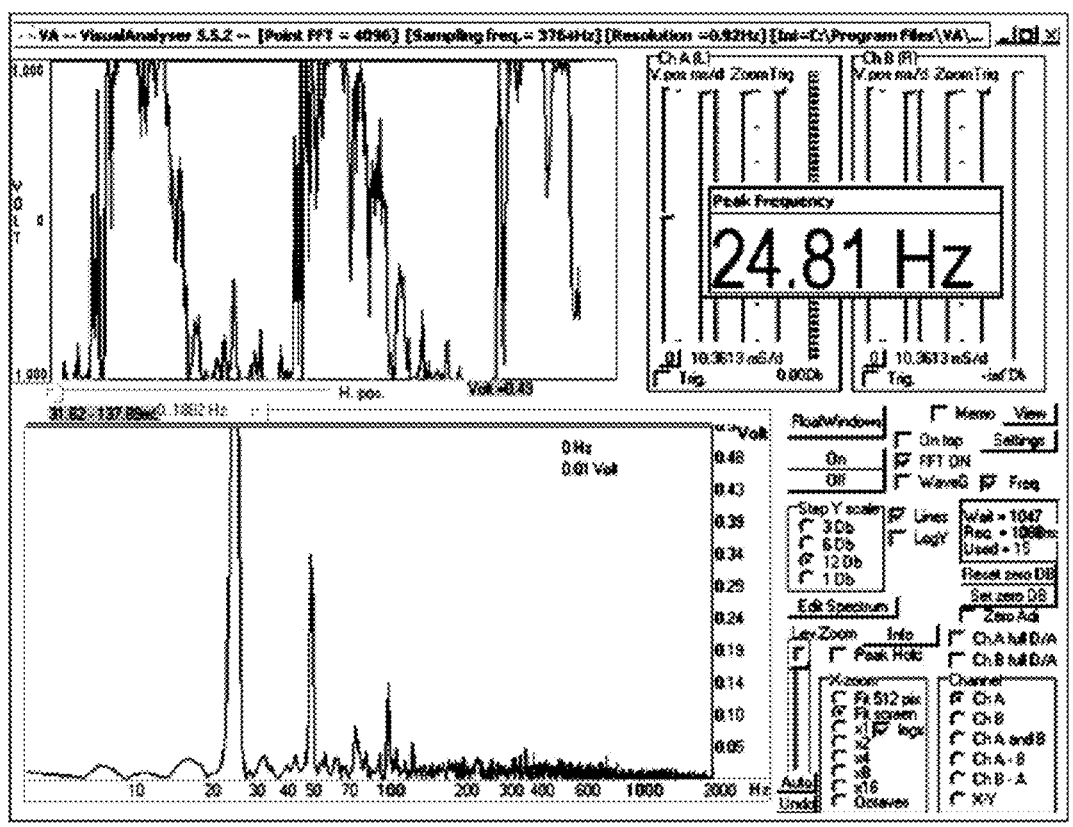
FIG. 13 present characterizes a power spectrum of the response to the device.

In FIG. 13, a power spectrum of the response to the device are shown.

Experiment 3: Assessment of the Immediate and Longer-Term Effects of Treatment with PulseHaler™ Cardio-Pulmonary Device on Patients with COPD (2009)

Abstract: PulseHaler™ is a novel device for administering pulsating air flow according to predetermined protocols that control air flow and pulsations—frequency, pressure amplitude, duration and waveform, affecting body tissues and organs and tailored to specific clinical conditions. This is an intermediate report of a clinical study conducted on 30 COPD patients, to measure the effect of the PulseHaler device on their physical capacity and quality of life. Patients were treated with PulseHaler for two weeks, 3 times per day, 22 minute each time according to the device's protocol. Patients were instructed to continue with the medication regime recommended by their physician. Measurements of respiratory functions, systemic effects, exercise capacity and quality of life were record before starting the treatment (for baseline), after the first treatment session (to study the immediate effect), and then after one week and two weeks (to measure the effect of a prolonged treatment) and after two weeks of non-treatment (the After Period). Initial data on 4 patients shows a pattern of strong positive response to treatment, including up to 40% improvement in 6 Minute Walk distance, between 5% and 13% improvement in FEV1, significant improvement in the oxygen saturation at rest and at exercise and an improvement in the patients' quality of life important to their daily life. This pattern entails both the immediate effect and its continuation in the prolonged 2-week treatment.

Methods: Patients diagnosed with Moderate to Very Severe COPD (FEV1<70%) are treated with PulseHaler for two weeks, 3 times per day, according to the 22-minute treatment protocol of the device. We studied the effect of treatment on lung functions (full spirometry, plethysmography, diffusion capacity), exercise capacity (6 minute walk test and oxygen saturation), quality of life (McMaster's Chronic Respiratory Questionnaire—CRQ-SAS) and on blood pressure and pulse. Parameters were measured for baseline before the first treatment, after it, after one and two weeks of treatment; Last measurements were taken after two more weeks of non-treatment, to study the fade-out effect of the treatment. Patients were then underwent an identical study protocol with a placebo device—a PulseHaler that provides continuous air stream only. In this cross-over study, 50% of patients are allocated randomly to be studied first with the placebo device and only then with the true PulseHaler device.

Results: By the time of writing this summary, one patient (p1) has completed the full treatment protocol, a two more patients (p2, p3) have completed two weeks of treatment, and a fourth patient (p4) has completed the first few days of the two-week treatment period.

A longitudinal view of all parameters of patient 1, a 74 years old man with severe COPD (FEV1=48% of predicted value), over the duration of the study (Table 6) shows a pattern of positive effect of the device on the corresponding area of wellness throughout the duration of the treatment period. The immediate effect of a single 22-minute treatment session elicited 40 meters improvement in the 6 Minute Walk test, arise of more than 10%. During the two-weeks period of treatment, a significant improvement of the FEV1 was recorded—a rise of 11% from baseline to the maximal value throughout the treatment period. An ever more marked elevation of 40% (135 meters) was recorded for the 6 Minute Walk test. The quality of life questionnaire shows an important improvement for the daily life of the patient, estimated as moderate to large magnitude, in the two emotional scores. During the two-week After (non-treatment) Period of the study some parameters continued to improve, while others were steady or even declined.

TABLE 6

Longitudinal view of the progress of the values of parameters over the study period (patient p1)

| | Baseline | Immediate Effect | Two-Weeks Max. Effect | 2-Weeks After | Two Weeks Max. Effect (Change*) | |
|---|---|---|---|---|---|---|
| FEV1 (liters) | 1.14 | 1.10 | 1.27 | 1.36 | 0.13 | 11% |
| FEV1 (% predicted) | 47 | 46 | 53 | 57 | 6 | 13% |
| Six M.W. (meters) | 335 | 375 | 470 | 400 | 135 | 40% |
| SaO2, pre-test (%) | 90 | 93 | 93 | 93 | 3 | 3% |
| SaO2, post-test (%) | 90 | 91 | 92 | 93 | 2 | 2% |
| CRQ - Dyspnea | 6.2 | | 6.3 | 6.0 | 0.0 | |
| CRQ - Fatigue | 5.0 | | 4.3 | 5.0 | −0.8 | |
| CRQ - Emotional | 4.4 | | 6.0 | 5.3 | 1.6 | |
| CRQ - Mastery | 5.5 | | 6.8 | 5.8 | 1.3 | |

Chart 24 presents a longitudinal view of lung functions and Six M.W. test (patient p1).

Chart 25: presents a longitudinal view of the McMaster's Chronic Respiratory Questionnaire (patient 1)

A view of the data for patient 2, a 71 years old man with moderate COPD (FEV1=62% of predicted value), depicted in table 7, shows a similar improvement pattern in FEV1 and the 6-Minute Walk distance, with 12% and 36% in them, respectively. Here the quality of life questionnaire shows significant improvement in the physical scores also—the dyspnea score rose by more than 0.5 (i.e., an important change for the daily life of the patient) and the fatigue score rose by 0.75 (important changes of moderate magnitude).

TABLE 7

Longitudinal view of the progress of the values of parameters over the study period (patient p2)

|  | Baseline | Immediate Effect | Two-Weeks Max. Effect | Two Weeks Max. Effect (Change*) | |
| --- | --- | --- | --- | --- | --- |
| FEV1 (liters) | 1.79 | 1.95 | 2.01 | 0.22 | 12% |
| FEV1 (% predicted) | 62 | 68 | 69 | 7 | 11% |
| Six M.W. (meters) | 320 | 434 | 434 | 114 | 36% |
| SaO2, pre-test (%) | 91 | 93 | 93 | 2 | 2% |
| SaO2, post-test (%) | 93 | 94 | 94 | 1 | 1% |
| CRQ - Dyspnea | 4.6 |  | 5.2 | 0.60 |  |
| CRQ - Fatigue | 3.5 |  | 4.3 | 0.75 |  |
| CRQ - Emotional | 4.9 |  | 4.9 | — |  |
| CRQ - Mastery | 4.0 |  | 4.8 | 0.75 |  |

Patient 3 is a 79 years old man with moderate COPD. This patient had similar trends of improvement: FEV1 rose by 4%, and the 6 Minute Walks distance—by 24%. Oxygen saturation at exercise rose also significantly for this patient, from 86% at baseline to 90%.

TABLE 8

Longitudinal view of the progress of the values of parameters over the study period (patient p3)

|  | Baseline | Immediate Effect | Two-Weeks Max. Effect | Two Weeks Max. Effect (Change*) | |
| --- | --- | --- | --- | --- | --- |
| FEV1 (liters) | 1.82 | 1.88 | 1.89 | 0.07 | 4% |
| FEV1 (% predicted) | 64 | 67 | 67 | 3 | 5% |
| Six M.W. (meters) | 275 | 248 | 340 | 65 | 24% |
| SaO2, pre-test (%) | 93 | 91 | 91 | −2 | −2% |
| SaO2, post-test (%) | 86 | 90 | 90 | 4 | 5% |
| CRQ - Dyspnea | 5.2 |  | 5.4 | 0.2 |  |
| CRQ - Fatigue | 4.0 |  | 3.0 | −1.0 |  |
| CRQ - Emotional | 5.9 |  | 5.7 | −0.1 |  |
| CRQ - Mastery | 4.8 |  | 4.8 | — |  |

Patient 4, a 65 years old woman with moderate COPD (FEV1=61% of predicted value, completed the first few days of treatment by the time of this report, therefore data is available for this patient only for the immediate effect. Here there was no significant change of the FEV1. However, an improvement of 10% (50 meters) in the 6 Minute Walk test was recorded together with a 6% improvement in the oxygen saturation at exercise.

TABLE 9

Longitudinal view of the progress of the values of parameters over the study period (patient p4)

|  | Baseline | Immediate Effect |
| --- | --- | --- |
| FEV1 (liters) | 1.11 | 1.09 |
| FEV1 (% predicted) | 48 | 47 |
| Six M.W. (meters) | 500 | 550 |
| SaO2, pre-test (%) | 94 | 94 |
| SaO2, post-test (%) | 91 | 97 |

Conclusion: In this intermediate analysis the data depicts a pattern that comprises (i) an improvement of pulmonary functions (FEV1), oxygen saturation at rest and at exercise, and exercise capacity (6-minute walk distance) following a single 22-minute treatment with the PulseHaler device; (ii) a continuation of that trend accompanied by an improvement of the quality of life during a 2-week, 3-times-per-day treatment course; and (iii) a mixed trend during the period after treatment stopped. These data support the hypothesis that the PulseHaler device has a positive effect on the overall physical capacity and quality of life. We assume that this is due to the effect of the device on the lungs and on the heart; where systemic functions, such as the 6 Minute Walk test and the oxygen saturation improved significantly without a comparable improvement of the FEV1 we assume that the improvement is due to the effect of the device on the cardiovascular system. As these data represent the study on 4 patients, further data is required to establish these conclusions.

The invention claimed is:

1. An air delivery device for applying a plurality of fluid pressure pulses of air to the airways of a patient for improving patient's health comprising:
   a. a cassette comprising an electric motor; an air tube attached to said cassette and comprising an input port and an output port;
   b. an airstream source fluidly coupled to said input port and delivering an airstream to said air tube; a disc located in proximity to said output port and comprising at least one cutout, and
   c. a mouthpiece fluidly coupled to said output port and adapted to apply said plurality of fluid pressure pulses to patients' airways,
   wherein said electric motor is mechanically coupled to said disc and spins said disc such that said airstream is occluded in accordance with a predetermined protocol thereby generating said plurality of fluid pressure pulses, and
   wherein said plurality of fluid pressure pulses comprises fluid pressure pulses of at least two different frequencies.

2. The air delivery device according to claim 1, wherein said cassette further comprises a controller configured to control the rotation of said electric motor thereby generating said plurality of fluid pressure pulses in accordance with said predetermined protocol.

3. The air delivery device according to claim 2, wherein said plurality of pressure pulses is delivered to patient's airways in accordance with patient's breathing rhythm said delivery of said plurality of pressure pulses is selected from the group consisting of delivering said plurality of fluid pressure pulses synchronously with patient's breathing rhythm and delivering said plurality of fluid pressure pulses asynchronously with patient's breathing rhythm.

4. The air delivery device according to claim 2, wherein said plurality of pressure pulses is delivered to patient's airways in accordance with patient's cardiac cycle said delivery of said plurality of pressure pulses is selected from the group consisting of delivering said plurality of fluid pressure pulses synchronously with patient's cardiac cycle and delivering said plurality of fluid pressure pulses asynchronously with patient's cardiac cycle.

5. The air delivery device according to claim 2, wherein said controller further comprises: at least one sensor for measuring at least one health related parameter of patient; a database storage microprocessor for storing and updating health related data; at least one analyzing means configured to: analyze at least one health related parameter; compare at least one health related parameter with said stored health related data; select said predetermined protocol from a repertoire of protocols in accordance with said comparison, said repertoire of protocols is stored in a CPU, and instruct said electric motor to spin said disc to generate said fluid pressure pulses in accordance with said predetermined protocol.

6. The air delivery device according to claim 1, wherein said plurality of fluid pressure pulses comprises at least one sequence of fluid pressure pulses.

7. The air delivery device according to claim 1, wherein said plurality of fluid pressure pulses is delivered to patient's airways said delivery of said plurality of fluid pulses is selected from the group consisting of delivering said fluid pressure pulses contemporaneously with patient's breathing inspirations and breathing expirations and delivering said fluid pressure pulses independently of patient's breathing inspirations and breathing expirations.

8. The air delivery device according to claim 1, wherein said predetermined protocol comprises at least one fluid pressure pulse frequency said pulse frequency is selected from the frequency group consisting of: from about 0.5 Hz to about 5.0 Hz; from about 5.0 Hz to about 10 Hz; from about 10 Hz to about 20 Hz; from about 20 Hz to about 30 Hz; from about 30 Hz to about 40 Hz; from about 40 Hz to about 50 Hz; from about 50 Hz to about 60 Hz; from about 60 Hz to about 70 Hz; from about 70 Hz to about 80 Hz; from about 80 Hz to about 90 Hz; from about 90 Hz to about 100 Hz, and any multiples thereof.

9. The air delivery device according to claim 1, wherein said predetermined protocol comprises a pulse amplitude, a pressure waveform and a protocol time duration, wherein said pulse amplitude is selected in accordance with clinical efficacy, wherein said pressure waveform is selected from the group consisting of:

a. $P(t) = A\sin^{-1}(\sin(\omega_1 t)) + B \times \theta(\sin(\omega_2 t)) + C$ where $\theta(t)$ is the *Heaviside* step function $$\theta(x) = \begin{cases} 1; x \geq 0 \\ 0; x < 0; \end{cases}$$

b. $P(t) = A\sin^{-1}(\sin(\omega_1 t)) + B \times \theta(\sin(\omega_2 t)) + C$;

c. $P(t) = A\sin^{-1}(\sin(\omega_1 T)) + B\sin^{-1}(\sin(\omega_2 t)) + C$, and d. $P(t) = P_0 \text{erfc}\left(\dfrac{l^2}{Dt}\right)$ where constant A is in a range 10 mmHg≤A≤250 mmHg; constant B is in a range 10 mmHg≤B≤250 mmHg, and constant C is in a range −250 mmHg≤C≤250 mmHg, $\omega_1$ and $\omega_2$ are in a range 0.01 Hz≤$\omega_1$≤1 Hz, 0.1≤$\omega_2$≤10 Hz, respectively, and $P_0$ is a constant, D is the diffusion constant of air, t is the time, and l is the distance from a measuring point to said air delivery device, and wherein said protocol time duration is selected from the time duration group consisting of from about 1 second to about 30 minutes and from about 30 minutes to about 24 hours.

10. The air delivery device according to claim 1, wherein said sequences of fluid pressure pulses is accompanied by predetermined humming oscillations for stimulation of nitric-oxide production, said humming oscillations provided independently of said sequence of fluid pressure pulses.

11. The air delivery device according to claim 1, wherein said sequences of fluid pressure pulses is accompanied by predetermined humming oscillations for stimulation of nitric-oxide production, said humming oscillations provided contemporaneously with said sequence of fluid pressure pulses.

12. The air delivery device according to claim 1, wherein said air delivery device is adapted for improving patient's health and patient is suffering from at least one of the following ailments: cystic fibrosis; chronic obstructive pulmonary disease; asthma; pneumonia; pulmonary hypertension; nasal congestion; emphysema; interstitial fibrosis, pulmonary hypertension, sarcoidosis; bronchitis; asbestosis; radiation fibrosis; ARDS; sinusitis; pharyngitis; laryngitis; otitis media; lung tumors; coronary heart disease; cardiomyopathy (CM); hypertrophic CM; dilated CM; hypertensive CM; congestive heart failure; inflammatory heart disease; endocarditis; myocarditis; cardiac arrhythmias; atrial fibrillation; atrial flutter; supraventricular tachycardia; A-V blocks; systemic; hypertension; atherosclerosis; atherosclerosis of the carotid arteries; sleep apnea; fibromyalgia and any combination thereof.

13. The air delivery device according to claim 1, wherein said air delivery device is adapted for improving patient's health and patient is suffering from a heart disease said heart disease is selected from the group consisting of heart failure, congestive heart failure, pulmonary oedema, and any combination thereof.

14. The air delivery device according to claim 1, wherein said improvement in patient's health comprises determining at least one of the following: an improvement in patient's diffusion capacity as measured by the DLCO test; an improvement in patient's health as measured by the six minute walk test; an improvement in patient's health as measured by the incremental shuttle walking test; an improvement in patient's lung volumes as measured by Lung Plethysmography; an improvement in patient's quality of life as measured by an increase in the patient's score on the Chronic Respiratory Questionnaire scale compared to the patient's score prior to said treatment, an improvement in patient's health as determined by a pulmonary function test; an improvement in patient's health as determined by static lung volume; an improvement in patient's health as determined by a functional exercise capacity; an improvement in patient's health as determined by drug uptake; an improvement in patient's health as determined by heart function; an improvement in patient's health as determined by cardio vascular efficiency; an improvement in patient's health as determined by pulmonary blood pressure; an improvement in patient's health as determined by systemic blood pressure; an improvement in patient's health as determined by blood oxygenation; an improvement in patient's health as determined by nitric oxide production; an improvement in patient's health as determined by a Health Related Quality of Life Questionnaire and any combination thereof.

15. The air delivery device according to claim 1, wherein an improvement in patient's quality of life is measured by at least one of the following: an increase in said patient's score of at least about 10 points on the Karnofsky scale compared to the patient's score prior to said treatment; in patient's quality of life as measured by an increase in the patient's score of at least about 20 points on the Karnofsky scale compared to the patient's score prior to said treatment; an improvement in the patient's quality of life is measured by a questionnaire selected from the group consisting of: St. George's Quality of Life Questionnaire, the Karnofsky scale, the WHO QOL questionnaire and any combination thereof; by an improvement in measures of physical performance; by an improvement in measures of mental performance; by an improvement in measures of physical performance and mental performance; the RMSSD increases by at least 20% after said treatment; the SDNN increases by at least 10% after said treatment; the PNN50 increases by at least 5% after said treatment and any combination thereof and wherein said improvement in the patient's quality of life is measured by an improvement in the patient's symptoms as defined by the Karnofsky score selected from a group comprising of Bedridden to Symptomatic in bed >50% of day, Symptomatic, in bed >50% of day to Symptomatic, in bed <50% of day, or Symptomatic, in bed <50% of day to Symptomatic, fully ambulatory: Symptomatic, fully ambulatory to Asymptomatic, normal Function and any combination thereof.

16. A method for applying a plurality of fluid pressure pulses of air to the airways of a patient for improving patient's health comprising: providing a cassette comprising an electric motor; attaching an air tube to said cassette said air tube comprising an input port and an output port; delivering an airstream to said input port of said air tube; locating a disc having at least one cutout in proximity to said output port; instructing said electric motor to spin said disc to occlude said airstream in accordance with a predetermined protocol thereby generating said fluid pressure pulses, and applying said plurality of fluid pressure pulses to said patients' airways by means of coupling a mouthpiece to said output port, wherein said plurality of fluid pressure pulses comprises fluid pressure pulses of at least two different frequencies.

17. The method of applying a plurality of fluid pressure pulses of air according to claim 16, further comprising: measuring at least one health related parameter of patient by means of at least one sensor, and selecting said predetermined protocol from a repertoire of stored protocols in accordance with an analysis of patient's at least one health related parameter and a comparison of patient's measured at least one health related parameter and health related data stored on a database storage microprocessor.

18. The method of applying a plurality of fluid pressure pulses of air according to claim 16, further comprising controlling said spinning of said electric motor by means of a controller.

19. The method of applying a plurality of fluid pressure pulses of air according to claim 16, further comprising delivering said plurality of pressure pulses to patient's airways in accordance with patient's breathing rhythm said delivering is selected from the group consisting of delivering said plurality of fluid pressure pulses synchronously with patient's breathing rhythm and delivering said plurality of fluid pressure pulses asynchronously with patient's breathing rhythm.

20. The method of applying a plurality of fluid pressure pulses of air according to claim 16, further comprising delivering said plurality of pressure pulses to patient's airways in accordance with patient's cardiac cycle said delivery of said plurality of pressure pulses is selected from the group consisting of delivering said plurality of fluid pressure pulses synchronously with patient's cardiac cycle and delivering said plurality of fluid pressure pulses asynchronously with patient's cardiac cycle.

21. The method of applying a plurality of fluid pressure pulses of air according to claim 16, wherein said plurality of fluid pressure pulses is delivered to patient's airways said delivery of said plurality of fluid pulses is selected from the group consisting of delivering said fluid pressure pulses contemporaneously with patient's breathing inspirations and breathing expirations and delivering said fluid pressure pulses independently of patient's breathing inspirations and breathing expirations.

* * * * *